(12) United States Patent
Arai et al.

(10) Patent No.: US 8,145,286 B2
(45) Date of Patent: Mar. 27, 2012

(54) NONINVASIVE MEASURING DEVICE FOR SUBSTANCE IN BLOOD VIA NAIL AND A NAIL EVAPORATION DEVICE

(75) Inventors: Tsunenori Arai, Kanagawa (JP); Yuki Kawase, Kanagawa (JP); Yasunobu Oka, Kanagawa (JP); Narushi Ito, Tokyo (JP)

(73) Assignees: Keio University, Tokyo (JP); Tanita Corporation, Tokyo (JP)

( * ) Notice: Subject to any disclaimer, the term of this patent is extended or adjusted under 35 U.S.C. 154(b) by 1518 days.

(21) Appl. No.: 11/606,155

(22) Filed: Nov. 30, 2006

(65) Prior Publication Data
US 2007/0161877 A1    Jul. 12, 2007

(30) Foreign Application Priority Data

Nov. 30, 2005 (JP) .................................. 2005-346913
Nov. 28, 2006 (JP) .................................. 2006-320734

(51) Int. Cl.
*A61B 5/1455* (2006.01)
(52) U.S. Cl. ..................... 600/322; 600/316; 600/340
(58) Field of Classification Search ............... 600/310, 600/315, 316, 322, 331, 340, 365; 604/20; 606/9
See application file for complete search history.

(56) References Cited

U.S. PATENT DOCUMENTS

| | | | |
|---|---|---|---|
| 5,246,004 A | | 9/1993 | Clarke et al. |
| 5,830,132 A | | 11/1998 | Robinson |
| 5,885,211 A | * | 3/1999 | Eppstein et al. .............. 600/309 |
| 5,947,956 A | * | 9/1999 | Karell ................................ 606/9 |
| 6,018,673 A | * | 1/2000 | Chin et al. .................... 600/322 |
| 6,463,314 B1 | * | 10/2002 | Haruna ......................... 600/407 |
| 6,706,032 B2 | * | 3/2004 | Weaver et al. ................ 604/500 |
| 2003/0181847 A1 | * | 9/2003 | Bruno-Raimondi ............ 604/20 |
| 2003/0208169 A1 | | 11/2003 | Chaiken et al. |
| 2005/0043597 A1 | * | 2/2005 | Xie .............................. 600/315 |
| 2005/0187438 A1 | * | 8/2005 | Xie .............................. 600/310 |
| 2005/0209514 A1 | * | 9/2005 | Oshima et al. ................ 600/310 |

FOREIGN PATENT DOCUMENTS

| WO | WO-01/37722 A1 | 5/2001 |
|---|---|---|
| WO | WO-03/068197 A1 | 8/2003 |

* cited by examiner

*Primary Examiner* — Eric Winakur
*Assistant Examiner* — Chu Chuan (JJ) Liu
(74) *Attorney, Agent, or Firm* — Birch, Stewart, Kolasch & Birch, LLP

(57) ABSTRACT

A device and method for optically measuring a substance in blood using the nail as an optical window are provided. A device for optically measuring a test substance in blood by using the nail as an optical window and correcting or eliminating fluctuation of a measurement value based on optical characteristics of the nail plate, comprising irradiation means applying light within a wavelength range for measuring absorption by the test substance to the nail of a subject, detection means detecting light diffused/reflected from or transmitted through the body of the subject, and processing means processing a signal obtained by the detection means to convert the signal into a concentration of the test substance.

13 Claims, 37 Drawing Sheets
(3 of 37 Drawing Sheet(s) Filed in Color)

a b

Wavelength [μm]
Absorbance of glucose (d=0.75mm)

85mJ/cm², 
1000th irradiation

415mJ/cm², 
500 times irradiation

830mJ/cm² irradiation

Surface after irradiation at 226 mJ/cm$^{-2}$·pulse

NONINVASIVE MEASURING DEVICE FOR SUBSTANCE IN BLOOD VIA NAIL AND A NAIL EVAPORATION DEVICE

BACKGROUND OF THE INVENTION

1. Field of the Invention

The present invention relates to a device for optically analyzing a substance in blood using light and the nail as an optical window. The present invention also related to a device which for forming an orifice to administer a pharmaceutical composition for a cutaneous disease and/or a systemic disease via nail on the nail plate.

2. Background Art

Methods for measuring a blood glucose level by applying near infrared light through the skin and measuring transmitted light and scattered light of the near infrared light have been developed (see JP Patent Publication (Kokai) No. 10-325794 A (1998), JP Patent Publication (Kokai) No. 11-137538 A (1999), JP Patent Publication (Kokai) No. 2000-131322 A, JP Patent Publication (Kokai) No. 2003-245265 A, JP Patent Publication (Kokai) No. 2004-257835 A, JP Patent Publication (Kokai) No. 2004-321325 A, JP Patent Publication (Kokai) No. 11-216131 A (1999), JP Patent Publication (Kokai) No. 10-33512 A (1998)). The measurement of a blood glucose level using light has an advantage of offering less invasive and continuous measurement to a patient. However, recent studies on measurement of a blood glucose level with near infrared light by targeting the skin as a measurement site have reported that a measurement accuracy is up to ±25 to 50 mg/dl since light absorption by glucose is low (see K. Maruo, Applied Spectroscopy, vol. 57, No. 10, pp. 1236-44, 2003), in contrast to an effective measurement accuracy of glucose in practice: 100 mg/dl±10 mg. In particular, the measurement accuracy is low when a glucose level is as low as near 50 mg/dl. Therefore, it has been difficult to apply such a measurement device in order to prevent hypoglycemia. In addition, disturbing elements in the skin such as the adipose tissue and protein significantly affect the measurement. Therefore, it has been difficult to greatly improve measurement accuracy of a blood glucose level by applying near infrared light through the skin.

On the other hand, techniques to make holes on the nail plate for the treatment of a cutaneous disease such as a trichophytosis unguium and for using a nail as a drug delivering device to deliver a pharmaceutical composition systemically via nail orifices have been developed (U.S. Pat. No. 5,947,956, U.S. Pat. No. 4,180,058 and K. Maruo, Applied Spectroscopy, vol. 57 m no. 10, pp. 1236-44, 2003). However, a device which accurately makes a hole in a nail plate as deep as possible without damaging a nail bed has not been developed.

SUMMARY OF THE INVENTION

An object of the present invention is to provide a device and method for optically measuring a substance in blood (blood substance) by use of the nail as an optical window. Another object of the present invention is to provide a device and method for evaporating the nail plate by applying light generated from a coherent light source, such as laser light, to the nail plate in optically measuring a blood substance using the nail as an optical window. Further object of the present invention is to provide a device and method for partly removing the nail plate by evaporating the nail plate by applying light generated from a coherent light source to the nail plate, for forming an orifice (orifices) to administer a pharmaceutical composition for a cutaneous disease and/or a systemic disease via nail on the nail plate The present inventors paid attention to the fact that the nail bed has a high density of capillary vessel, and found that a blood substance can be measured through the nail by use of the nail plate as an optical window. The present inventors particularly found that a substance having an absorption in the near infrared region, such as glucose, can be measured by using near infrared light.

Furthermore, the present inventors monitored the contents of water and keratin of the nail plate, which affect optical measurement and found that the content of a blood substance can be accurately measured by correcting an optical measurement value based on the monitoring results. Based on the finding, the present invention was accomplished.

Furthermore, the present inventors conducted intensive studies on a method for removing effect of the nail plate upon optical measurement and found that the nail plate can be evaporated by applying light generated from a coherent light source such as laser light to the nail plate. Additionally, they studied specifically about the irradiation conditions of the light generated from a coherent light source and found the irradiation conditions under which the nail plate can be evaporated so as to accurately measure a blood substance in the capillary vessel of the nail bed portion. Based on the findings, they have accomplished not only a device and method for evaporating the nail plate with light generated from a coherent light source but also a device and method for accurately measuring a blood substance in the capillary vessel of the nail bed portion by applying light generated from a coherent light source to the nail plate to evaporate it.

The present inventors further accomplished a device and a method for forming an orifice (orifices) to administer a pharmaceutical composition for a cutaneous disease and/or a systemic disease via nail on the nail plate, by partly removing the nail plate with applying light generated from a coherent light source to the nail plate so as to evaporate the nail plate.

More specifically, the aspects of the present invention are as described below.

[1] A device for optically measuring a test substance in blood by using the nail as an optical window and correcting or eliminating fluctuation of a measurement value based on optical characteristics of the nail plate, comprising irradiation means applying light within a wavelength range for measuring absorption by the test substance to the nail of a subject, detection means detecting light diffused/reflected from or transmitted through the body of the subject, and processing means processing a signal obtained by the detection means to convert the signal a concentration of the test substance.

[2] The device according to item [1], in which the irradiation means and the detection means are contained in a probe, and light is applied by the irradiation means through the nail into the body of the subject and light diffused/reflected from the body of the subject is detected by the detection means through the nail.

[3] The device according to item [1] or [2], in which the irradiation means applying light within a wavelength range for measuring absorption by the test substance to the nail applies light to capillary vessel of the nail bed portion.

[4] The device according to any one of items [1] to [3], in which the irradiation means applying light within a wavelength range for measuring absorption by the test substance to the nail applies near infrared light.

[5] The device according to item [4], in which the wavelength range of the light to be applied is 1 to 2.5 μm.

[6] The device according to any one of items [1] to [5], in which the device is a blood glucose level measuring device.

[7] The device according to any one of items [1] to [5], in which the device is used for measuring blood urea, creatinine, BUN, or CP (creatinine phosphokinase).

[8] The device according to any one of items [1] to [7], further comprising monitor means, which monitors a water content and a keratin content of the nail by using light within a wavelength range for measuring absorption by water in the nail and light within a wavelength range for measuring absorption by keratin in the nail, and which is capable of correcting optical characteristics of the nail plate.

[9] The device according to item [8], in which the monitor means uses light having a wavelength of 1 to 3 μm as the light within a wavelength range for measuring absorption by water in the nail and light having a wavelength of 1 to 2.5 μm as the light within a wavelength range for measuring absorption by keratin in the nail.

[10] The device according to any one of items [1] to [9], further comprising means for immobilizing/holding a finger tip portion, in which the immobilizing/holding means has the irradiation means and the detection means.

[11] The device according to any one of items [1] to [10], further comprising a nail plate evaporation device, which partly removes the nail plate by evaporating the nail plate by applying light generated from a coherent light source to the nail plate, for optically measuring a test substance in blood in the nail bed portion by using the nail as an optical window and correcting or eliminating a fluctuation of a measurement value based on optical characteristics of the nail plate, and which comprises a evaporation depth monitor means having irradiation means applying light generated from a coherent light source to the nail plate and light detection means detecting fluorescence emitted from the nail plate and the dermis for monitoring evaporation depth of the nail plate.

[12] The device according to item [11], in which the coherent light source is ultraviolet laser light or OPO.

[13] The device according to item [12], in which the ultraviolet laser light is ArF laser light.

[14] The device according to any one of items [11] to [13], in which a pulse energy density of the laser is not less than 10 mJ/cm$^2$·pulse.

[15] The device according to any one of items [11] to [14], in which, in monitoring the evaporation depth of the nail plate, irradiation is performed with a fluence such that intensity of plume emission, which is simultaneously generated in a wavelength range of fluorescence generating during light irradiation for evaporation, is equal to or less than intensity of fluorescence emitted from the nail plate and/or the dermis.

[16] The device according to any one of items [11] to [15], further comprising means immobilizing/holding a finger tip portion, which has laser the light irradiation means and the light detection means of the evaporation depth monitor means.

[17] A nail plate evaporation device, which partly removes the nail plate by evaporating the nail plate by applying light generated from a coherent light source to the nail plate, for optically measuring a test substance in blood in the nail bed portion by using the nail as an optical window and correcting or eliminating a fluctuation of a measurement value based on optical characteristics of the nail plate, and which comprises a evaporation depth monitor means having irradiation means applying light generated from a coherent light source to the nail plate and light detection means detecting fluorescence emitted from the nail plate and the dermis for monitoring evaporation depth of the nail plate.

[18] A nail plate evaporation device, which partly removes the nail plate by evaporating the nail plate by applying light generated from a coherent light source to the nail plate, for forming an orifice (orifices) to administer a pharmaceutical composition for a cutaneous disease and/or a systemic disease via nail on the nail plate, and which comprises a evaporation depth monitor means having irradiation means applying light generated from a coherent light source to the nail plate and light detection means detecting fluorescence emitted from the nail plate and the dermis for monitoring evaporation depth of the nail plate.

[19] The device according to item [17] or [18], in which the coherent light source is ultraviolet laser light or OPO.

[20] The nail plate evaporation device according to item [19], in which the ultraviolet laser light is ArF laser light.

[21] The nail plate evaporation device according to any one of items [17] to [20], in which a pulse energy density of the laser is not less than 10 mJ/cm$^2$·pulse.

[22] The nail plate evaporation device according to any one of items [17] to [21], in which, in monitoring the evaporation depth of the nail plate, irradiation is performed with a fluence such that intensity of plume emission simultaneously generated in a wavelength range of fluorescence generating during light irradiation for evaporation is equal to or less than intensity of fluorescence emitted from the nail plate and/or the dermis.

[23] The nail plate evaporation device according to any one of items [17] to [22], further comprising means immobilizing/holding a finger tip portion which has laser light irradiation means and light detection means of evaporation depth monitor means.

The device of the present invention can measure a test substance in blood of a subject using the nail as an optical window. In particular, since the density of capillary vessel existing in the nail bed under the nail is high, the nail bed portion can be used as a measurement target to obtain information about optical characteristics of a test substance, with the result that measurement can be accurately performed. When a blood substance in the capillary vessel of the nail bed portion is optically measured through the nail, measurement of the blood substance is affected by optical characteristics of keratin and water contained in the nail. Use of a device having a monitoring means, which monitors a water content and a keratin content in the nail, by using light within the wavelength range for measuring absorption by water in the nail and light within the wavelength range for measuring absorption by keratin in the nail according to the present invention, makes it possible to computationally remove the effect of keratin and water contained in the nail, thereby accurately measuring the concentration of a blood substance. Furthermore, use of a device for evaporating the nail plate by light generated from a coherent light source makes it possible to remove the effect of optical characteristics of the nail plate, thereby accurately measuring the concentration of a blood substance.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 3-1 is an absorption spectrum of glucose;

FIG. 3-2 is an absorption spectrum of urea;

FIG. 3-3 is an absorption spectrum of creatinine;

DETAILED DESCRIPTION OF THE PREFERRED EMBODIMENTS

The present invention is directed to measuring a blood substance by irradiating the nail with near infrared light within a predetermined wavelength and measuring absorption of the near infrared light by the blood substance through the nail.

In the present invention, the nail is used as an optical window. The phrase "the nail is used as an optical window" means that light is applied through the nail for measuring a test substance in blood, or that light is applied through the nail within a subject's body for measuring a test substance in blood, in which the light is absorbed and scattered in the living body and goes again out of the subject's body through the nail and the absorbed and scattered light is detected through the nail. Furthermore, in the present invention, the concentration of a blood substance is accurately measured by correcting or eliminating fluctuation of a measurement value based on optical characteristics of the nail plate. The phrase "correcting or eliminating fluctuation of a measurement value based on optical characteristics of the nail plate" means that an optical measurement value obtained through the nail plate is corrected by eliminating a value fluctuated by absorption, scattering and reflection of light due to water and keratin contained in the nail plate from the optical measurement value, or means that the nail plate is partly removed so as not to contain a value fluctuated by absorption, scattering, and reflection of light due to water and keratin contained in the nail plate in the optical measurement value obtained through the nail plate to accurately measure a test substance in blood.

Figure 1:
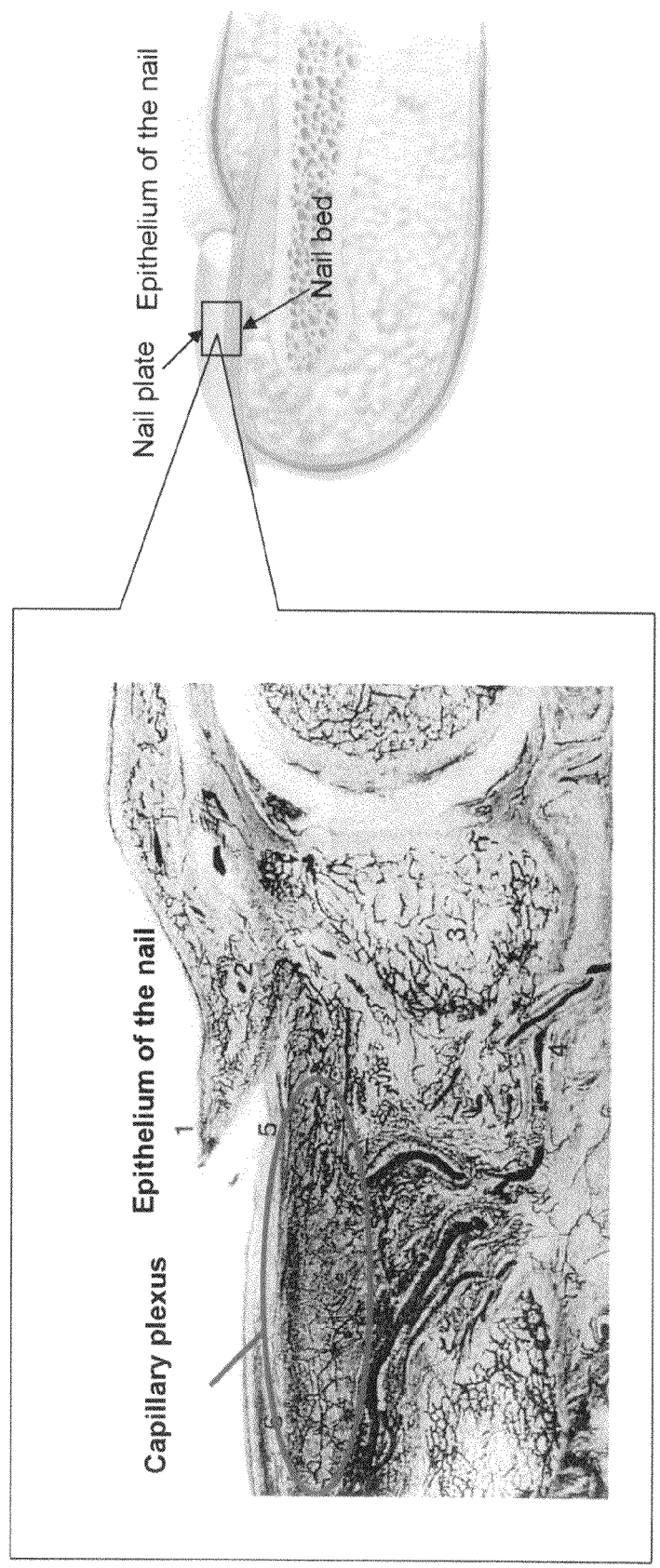
FIG. 1 is an illustration showing the structure of the nail plate and nail bed.
Figure 2:
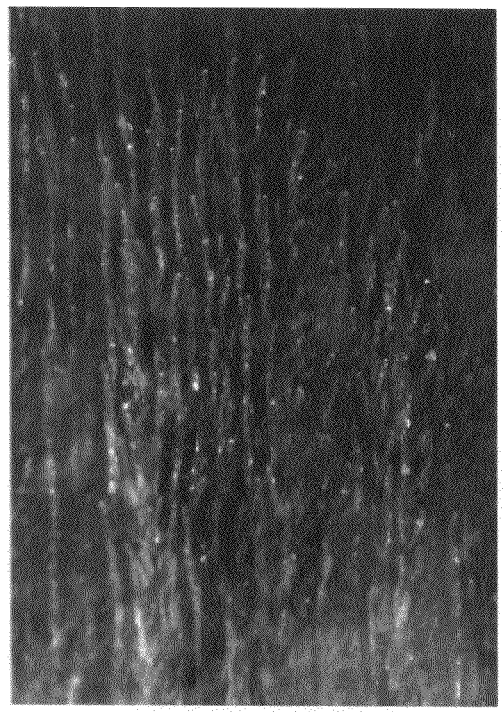
FIG. 2 is a microphotograph showing the capillary vessel under the nail.

Light applied through the nail goes into the subject's body and is absorbed and scattered by a test substance to be measured. In the present invention, diffused/reflected light, which is scattered and reflected from the subject's body and goes out of the subject's body through the nail, is measured. Since the present invention is directed to measuring a test substance in blood as a measurement target, the nail bed under the nail plate is used as a target site to detect the test substance. To explain more specifically, there is a high-density of the capillary vessel in the nail bed portion, which means that the amount of blood per unit volume is high. FIG. 1 shows the structure of the nail portion including the nail plate and the nail bed (Wolfram-gabel R. et al., J. Hand Surgery, vol. 20B, No. 4, pp 488-492, 1995, Thibodeau G. A., Anatomy/Physiology to study in color, Igaku-Shoin Ltd., pp 73, 1999). FIG. 2 shows the profile of the capillary vessel of the nail bed portion (Hasegawa K., J. Hand Surgery, vol. 26A, No. 2, pp. 283-290, 2001). The ratio of the area occupied by the capillary vessel under the nail is about 44%, which is significantly large compared to 3% in the upper arm and 7% in the palm (Pasyk K. A., Plastic and Reconstructive Surgery, vol. 83, No. 6, pp. 939-947). Therefore, a test substance in blood can be accurately measured by applying light to the nail bed portion as a target and measuring absorption of the light by the test substance existing in the capillary vessel of the nail bed portion. When the nail bed portion is targeted, since the nail bed portion is located at a depth of about 0.2 to 1 mm from the nail surface, irradiation light may be targeted at the depth. In addition, to increase the amount of blood of the portion under the nail irradiated with light, measurement may be performed while pressing a finger.

Figures 1, 3:
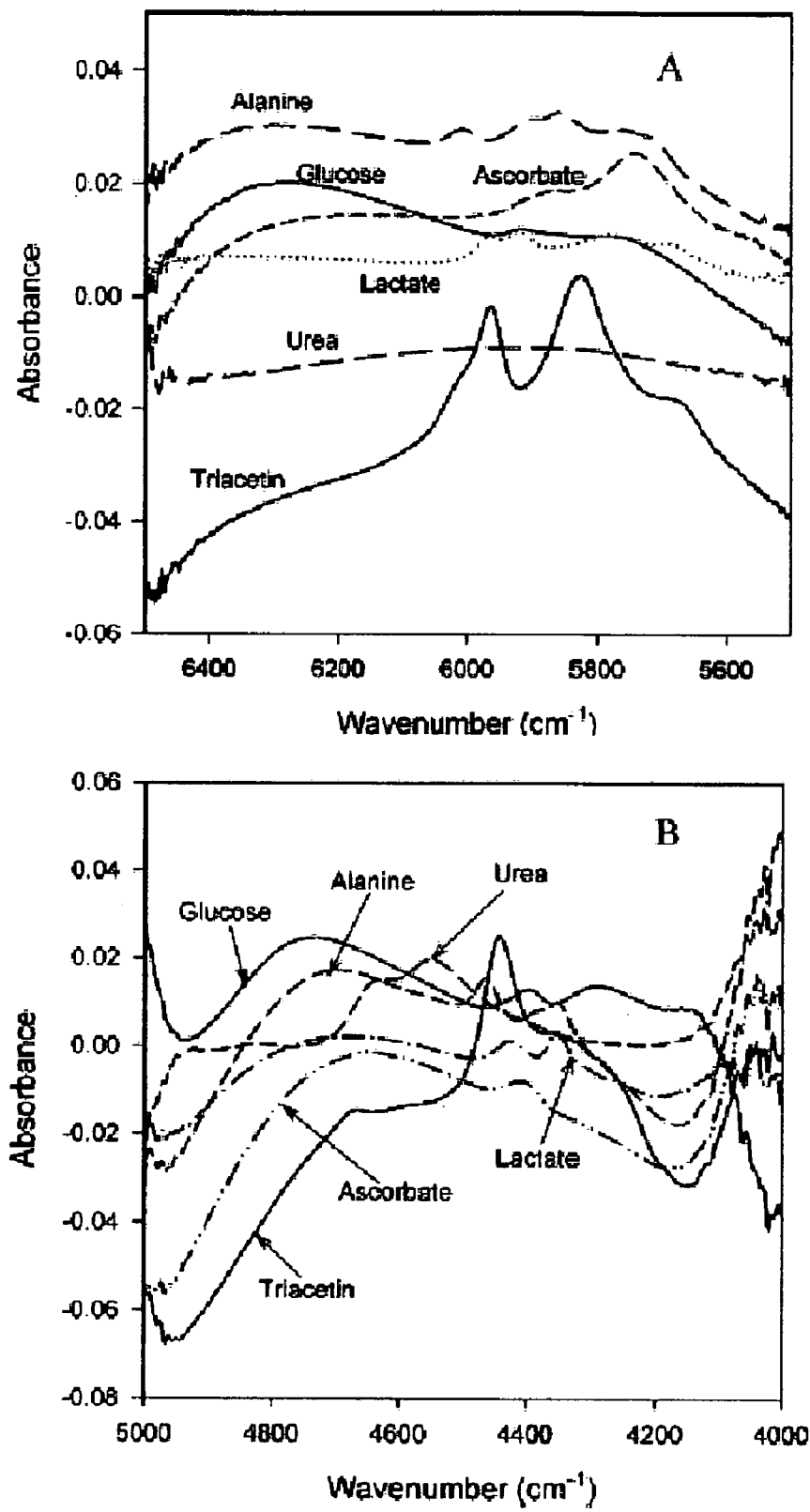
Figure 3:
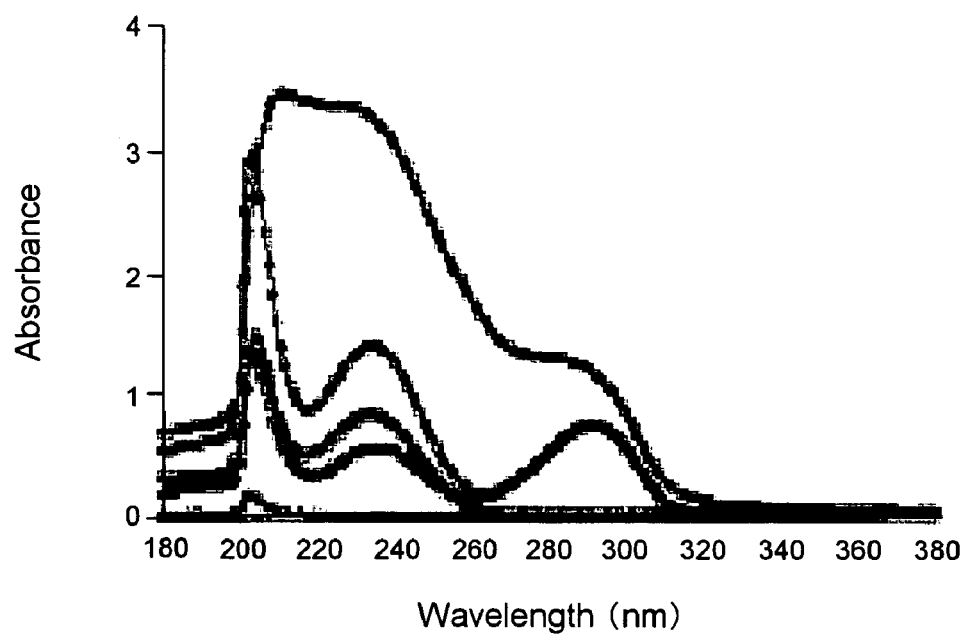
Figure 2:
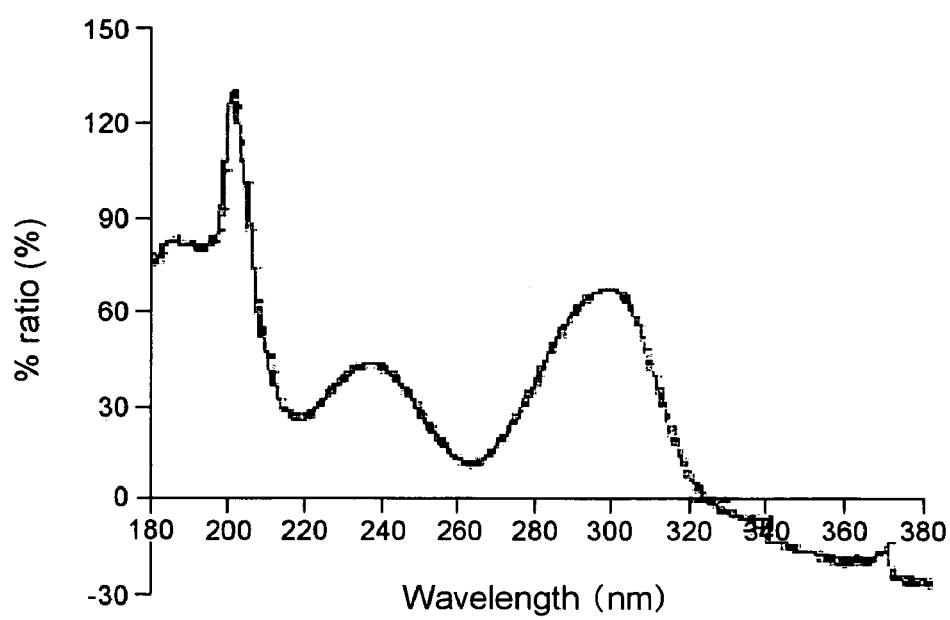
Figure 3:
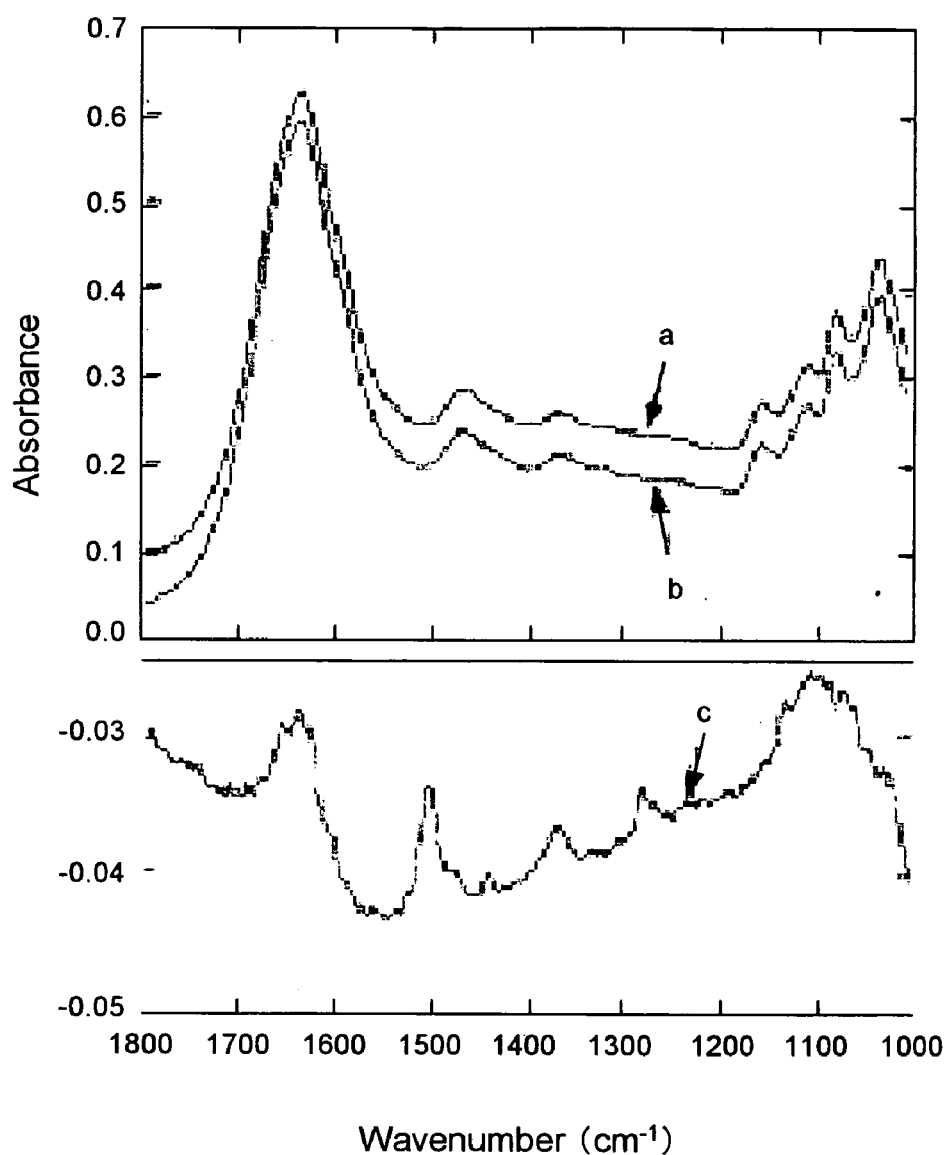

In the present invention, the test substance in blood to be measured is not limited and any substance may be used as a measurement target of the present invention as long as it can absorb light within a predetermined wavelength. Examples of such a substance include glucose, urea, creatinine, BUN (urea nitrogen) and CP (creatinine phosphokinase). The wavelength suitable for each of the test substances can be determined by measuring a light absorption spectrum of each test substance. FIGS. 3-1, 3-2 and 3-3 respectively show absorption spectra of glucose, urea (Mark A. et al., Small Anal. Chem. 2004, 76, 5405-5413) and creatinine (Fujii T. et al., Applied Spectroscopy, vol. 51, No. 11, 1682-1686, 1997, Fridolin I. et al., Medical and Biological Engineering and Computing, Vol. 41, 263-270, 2003). From these figures, the wavelengths can be appropriately selected. In this case, measurement is affected by absorption/scattering of light by disturbing elements such as water and protein existing in the nail or the living body of a subject. Therefore, light having a wavelength less absorbed by these disturbing elements is preferably used. For this reason, it is preferable to use near infrared light, which is less absorbed by water and a protein such as hemoglobin and highly capable of transmitting though a living body. The near infrared light used herein refers to light having a wavelength whose lower limit is about 0.76 to 0.83 µm and upper limit is 2.5 µm. In this respect, glucose and urea, which have a peak of absorption spectrum in the near infrared wavelength range, are suitably measured.

When near infrared light is used, the longer wavelength the near infrared light, more preferable. The wavelength is preferably 1 to 2.5 µm and further preferably 2 to 2.3 µm.

Note that correction of values may be performed by subtracting a measurement value obtained by applying light having a wavelength in which a test substance does not exhibit absorption, as a base. Measurement may be performed using light of a single wavelength at a single point or using a plurality of lights different in wavelength at a plurality of points. Furthermore, an absorption spectrum is measured in a predetermined wavelength range and a peak value and a base value of a test substance may be obtained from the absorption spectrum and used in correction. Alternatively, based on the absorption spectrum, regression analysis, such as multiple regression analysis, main component analysis and PLS method, may be performed.

The present invention encompasses a device and method for attaining accurate measurement by simultaneously measuring absorption/scattering by water and protein, thereby correcting a measurement value. In particular, when an optical measurement is performed through the nail, measurement may be likely affected by absorption/scattering of light by water and keratin in the nail. The nail, particularly, the nail plate contains water and keratin, which may affect measurement. To explain more specifically, the light measured through the nail reflects not only light absorption by a blood substance to be measured but also light absorption by components of the nail plate such as keratin and water. The latter light absorption affects the measurement value as noise.

Accordingly, it is necessary to monitor the contents of keratin and water in the nail plate so as to correct measurement values based on the monitoring results.

Figure 4:
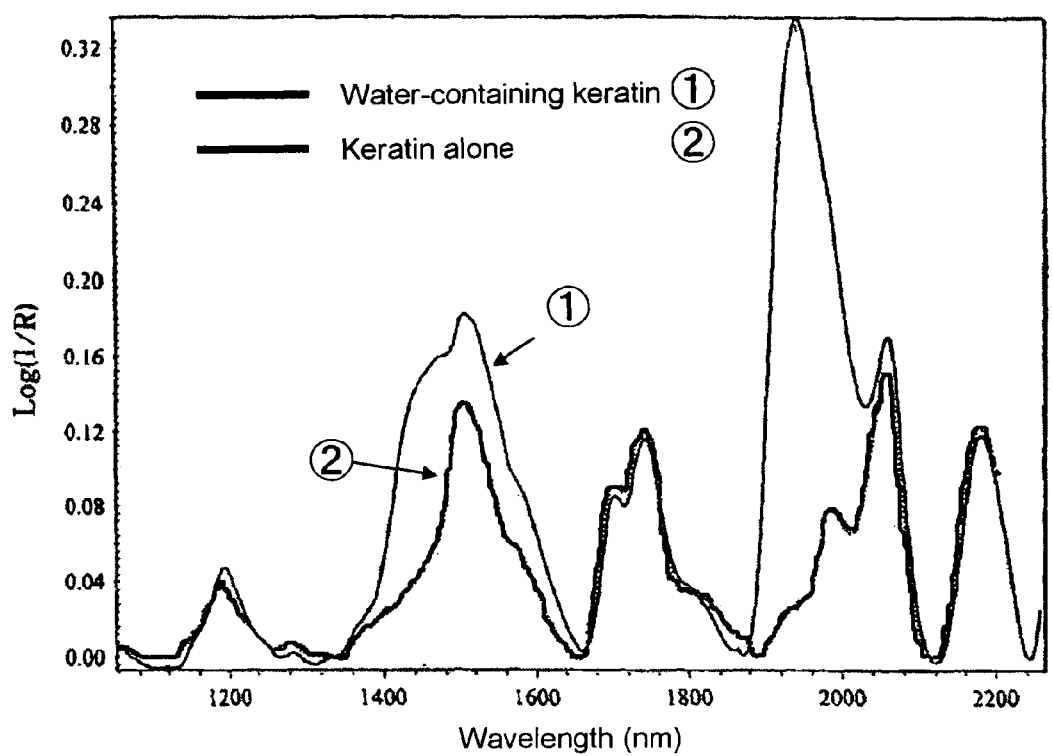
FIG. 4 is an absorption spectrum of keratin and water-containing keratin.

The contents of water and keratin in the nail plate can be measured respectively by use of light beams having wavelengths absorbed by water and keratin. The absorption spectra of keratin and keratin containing water are shown in FIG. 4 (Takashi Matsuzaki, Advanced Hair Science, Fragrance Journal Ltd. pp. 98, revised). Light having a wavelength of 1 to 3 µm is mentioned as to light falling within a wavelength range for measuring an absorption by water in the nail, whereas light having a wavelength of 1 to 2.5 µm is mentioned as to light falling within a wavelength range for measuring an absorption by keratin in the nail. In this case, the measurement value may be corrected by subtracting a measurement value by light within the wavelength range in which water and keratin show no absorption, as a base. Light having such a wavelength can be appropriately selected based on the absorption spectra shown in FIG. 4. Measurement may be performed using light of a single wavelength at a single point or using a plurality of lights different in wavelength at a plurality of points. Furthermore, an absorption spectrum is measured in a predetermined wavelength range to obtain a peak value and a base value of a test substance from the absorption spectrum. Measurement values may be corrected by use of these values. Alternatively, based on the absorption spectrum, regression analysis, such as multiple regression analysis, main component analysis and PLS method, may be performed.

Figure 5:
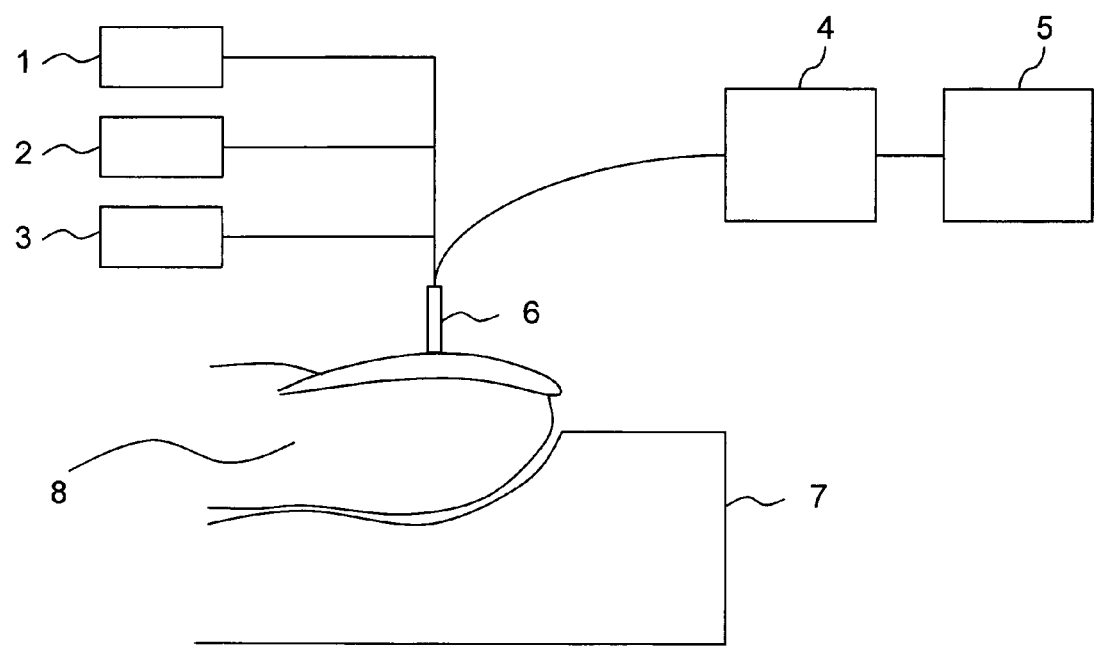
FIG. 5 shows a device for measuring the water content of the nail using three light sources different in wavelength.

A constitution of the monitoring means of the present invention is shown in FIG. 5. As shown in FIG. 5, the monitoring means uses three light beams different in wavelength corresponding to water absorption, keratin absorption and base absorption. Light is guided by way of an optical fiber to the nail and applied to the nail. Transmitted light or reflected light thereof is detected by an optical detection unit 4. In this case, a light irradiation means and a light detection means may be housed in a probe 6. The measurement value is corrected by a processing unit 5 in consideration of optical characteristics of the nail plate due to keratin and water contained in the nail plate. In this manner, measurement can be accurately performed.

The contents of water and keratin in the nail plate may be measured at the same time or before a test substance in blood is measured.

The absorbance finally obtained reflects absorbance of a test substance in blood, absorbance of keratin and absorbance of water existing in the nail plate. Therefore, correction is performed by subtracting the absorbance of keratin and the absorbance of water existing in the nail plate. At this time, the keratin content in the nail plate varies among persons and the water content in the nail plate also varies among persons and depending upon the ambience humidity, etc. Therefore, correction by the keratin content and the water content is performed preferably every time a test substance in blood is measured.

Furthermore, in the optical measurement according to the present invention, the nail is used as an optical window. In measurement, disturbing elements concerning the nail can be eliminated by applying various treatments to the nail.

For example, the effect of surface roughness of the nail plate on optical characteristics can be eliminated by polishing the surface of the nail plate by sandpaper. Polishing may be performed so as to obtain a surface roughness of 0.2 µm or less, preferably 0.1 µm or less, in terms of Ra (arithmetic average). When the nail plate is polished, it is only necessary to polish the area of the nail plate to be irradiated with light, for example, the area in contact with a probe. To correct optical characteristics within the nail plate, the nail plate may be impregnated with a chemical agent for adjusting an index of refraction such as glycerin. In this way, light scattering by the nail plate can be reduced.

Furthermore, measurement light can be applied directly to the nail bed by partly reducing the nail plate in thickness or forming a hole in the nail plate to expose the nail bed. In this manner, a test substance in blood can be measured without being affected by water and keratin of the nail plate.

As a method of partly reducing the nail plate in thickness or forming a hole in the nail plate, for example, a method of evaporating the nail plate may be mentioned. In this method, the nail plate is irradiated with light generated from a coherent light source such as laser light to evaporate the nail plate. Examples of the light generated from a coherent light source include ultraviolet pulse lasers such as ArF laser, XeCl laser and XeF laser, and OPO (optical parametric oscillator). Irradiation may be performed by transmitting light generated from a coherent light source through an optical system such as a lens and by applying the light to the nail plate surface in a desired pulse irradiation energy density. In this case, the light generated from a coherent light source may be transmitted by way of an optical transmission fiber such as a quartz fiber from the light source to the optical system.

The pulse energy density of the light generated from a coherent light source to be applied to the nail plate is preferably 10 mJ/cm$^2$ or more.

Figure 6:
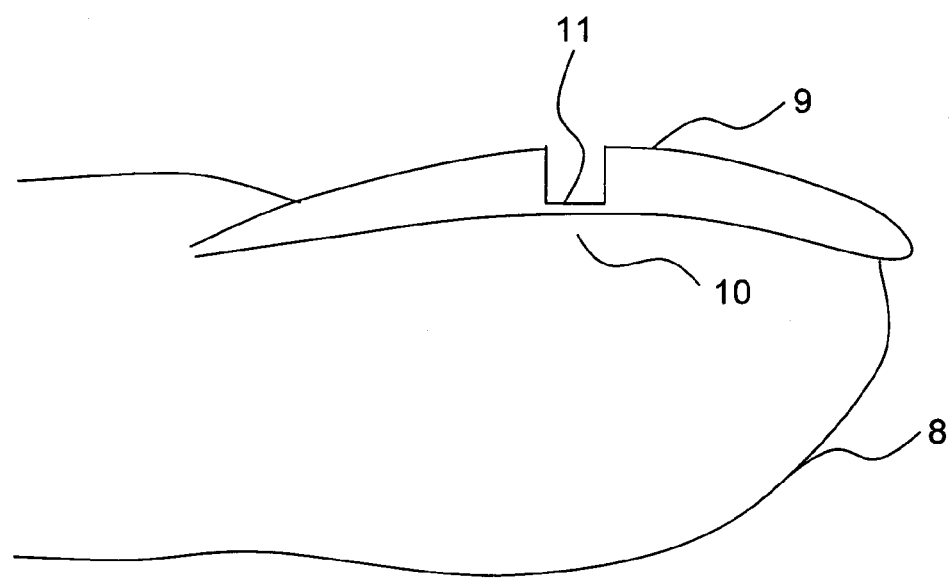
FIG. 6 is a view of the nail plate on which a hole is formed by evaporation of the nail plate.
Figure 7:
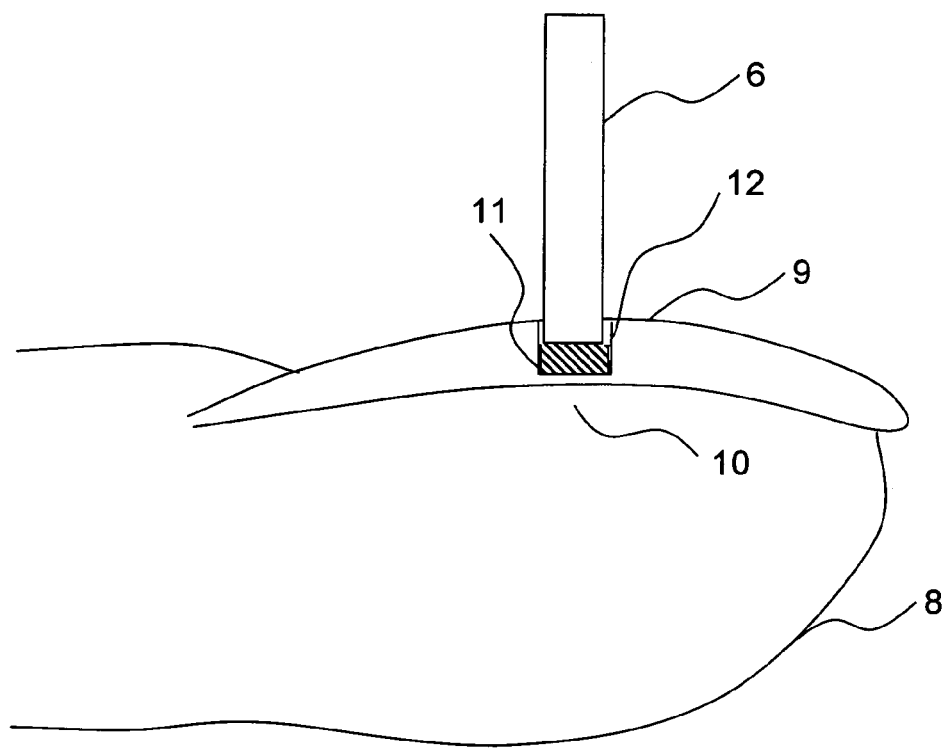
FIG. 7 is a method of measuring a blood substance by use of a hole formed by evaporation of the nail plate.

The area of the nail plate to be evaporated is not limited. However, in some cases, a blood substance is measured through a part of the nail plate evaporated by inserting a probe for measuring a blood substance into the evaporated nail plate. Therefore, the area to be evaporated is good enough for the probe to enter. The shape of the hole to be formed by evaporating the nail plate is also not limited. The shape of the hole to be evaporated may be rectangular and circular, etc. FIG. 6 shows the nail plate 9 having a hole 11 formed by evaporating the nail plate. As is shown in the figure, the nail plate of the hole 11 is thin. When a blood substance in the capillary vessel of the nail bed portion 10 is optically measured through the hole, measurement can be performed accurately without adverse affect of the nail plate. FIG. 7 shows an optical measurement method for measuring a blood substance in the capillary vessel of the nail bed portion through the hole of the nail plate formed by evaporation. As is shown in FIG. 7, a probe 6 is inserted in the hole 11 formed in the nail plate 9 by evaporation and receives diffused/reflected light from the nail bed 10. To suppress reflection between the nail and the probe, measurement is preferably performed via an index of refraction adjusting medium 12 inserted between the nail and the probe. As the index of refraction adjusting medium, glycerin or the like may be mentioned.

The device of the present invention can be used as a device for forming an orifice (orifices) to administer a pharmaceutical composition for a cutaneous disease and/or a systemic disease via nail on the nail plate. A subject animal in which an orifice (orifices) is formed on a nail plate to administer a pharmaceutical composition includes any animal including a human having nails. The cutaneous disease is not limited, but includes any cutaneous disease such as a cutaneous disease of a nail and a cutaneous disease of a skin other than a nail. A cutaneous disease of a nail includes a trichophytosis unguium which is a ringworm of a nail. A systematic disease is not also limited, but includes any disease known as a disease. The pharmaceutical composition for a cutaneous disease and/or a systemic disease includes a drug used for prophylaxis of a disease such as vaccine. When an orifice (orifices) is formed by the present device and a pharmaceutical composition is administered in the orifice (orifices), the pharmaceutical composition is delivered to not only a nail portion but also an entire body via capillary located at a nail bed portion. Accordingly, the administration via a nail takes effects on a systematic disease.

When an orifice (orifices) to administer a pharmaceutical composition for a cutaneous disease and/or a systemic disease via nail is formed, the depth of the orifice (orifices) is 80 to 100%, preferably 90 to 99% of the thickness of a nail plate. The diameter of the orifice is preferably, 1 µm to 1 mm, more preferably 50 µm to 200 µm, and the most preferably 50 µm to 100 µm. The orifice shape is preferably columnar shape or conical shape. Typically, about 500 orifices, for example, about 50 to 400 orifices or 100 to 300 orifices are formed on the nail.

The pharmaceutical composition of the present invention contains at least one active ingredient. For the purpose of the present invention, the active ingredient means any substance which result in pharmaceutical or therapeutic effects. An active ingredient is not limited, but includes photosensitizer, antifungal drug, androgen, estrogen, nonsteroidal anti-inflammatory drug, anti-hypertension drug, analgesic drug, antidepressant drug, antibiotic drug, anti-cancer drug, anesthetic, antiemetic drug, anti-infection drug, anti-diabetes drug, steroid, antiallergic drug, migrane-abortive drug, a drug for quitting smoking, and anti-obesity drug.

The pharmaceutical composition above may contain 1 type or a plurality of types of physiologically acceptable pharmaceutical additives such as a diluent, a preservative, a solubilizing agent, an emulsifier, an adjuvant, an antioxidant, an isotonizing agent, an excipient, and a carrier. Examples of an appropriate carrier include, but are not limited to, a physiological saline solution, phosphate buffered saline, a phosphate buffered saline glucose solution, and a buffered saline solution. Furthermore, the composition may also contain a stabilizer, such as amino acids, sugars, a surfactant, or an agent for preventing adsorption to the surface, which are known in the art. Examples of such form of a pharmaceutical composition include a liquid, solid, gel, emulsion, a liquid, and the like. The amount to be administered can be appropriately determined depending on the kind of disease, the kind of the active ingredient, and the size and the number of the orifice.

The orifice may be covered with a resin film, manicure and the like such that a pharmaceutical composition in the orifice does not come out from the orifice and bacteria, dust and the like do not mix in the orifice after the pharmaceutical composition is administered in the orifice.

The evaporation depth of the nail plate, in other words, the depth of the hole, can be measured by monitoring fluorescence emitted from the nail plate and the dermis under the nail when light generated from a coherent light source is applied. In this case, it is preferable to employ a coherent light source as a light source for use in monitoring the fluorescence. This is because when the evaporation depth is shallow, a large amount of fluorescence is emitted from a substance largely contained in the nail, such as keratin. In contrast, when the evaporation depth is deep, that is, the nail plate becomes thin, the amount of fluorescence emitted from the substance contained in the nail plate decreases, whereas the amount of fluorescence emitted from a substance contained in a large amount in the dermis, such as collagen, increases. The fluorescence from the nail plate and the fluorescence from the dermis can be distinguishably measured by measuring the wavelength around the peak of the fluorescence from the nail plate and the wavelength around the peak of the fluorescence from the dermis. For example, when the fluorescence from keratin of the nail plate is compared to that derived from collagen of the dermis by using ArF laser as a light source for monitoring fluorescence, the wavelength spectra of the fluorescence of both substances are analogous and can be measured at near a wavelength of 300 to 350 nm; however, fluorescence from the dermis is twice or more as larger as that from keratin of the nail plate. Therefore, as the evaporation depth of the nail plate increases and the nail plate reduces in thickness, the intensity of fluorescence increases. Thus, the evaporation depth of the nail plate can be monitored by measuring a change of the intensity of fluorescence. To measure fluorescence in order to monitor the evaporation the depth of the nail plate, a fluorescence probe having a fluorescence receiving portion may be used. The probe may have a means applying light generated from a coherent light source for evaporation.

When the nail plate is evaporated by applying light generated from a coherent light source, particles called plume are released by evaporation and light is also emitted from the plume. These phenomena may affect monitoring of the evaporation depth of the nail plate. To avoid the effect of plume emission, it may be necessary to reduce the amount of plume released. To attain this, when fluorescence is monitored, the pulse energy density of light generated from a coherent light source and to be applied to the nail plate may be set at a predetermined value or less.

A method of reducing the nail plate in thickness is not limited to evaporation. The thickness of the nail plate may be reduced simply by polishing the nail plate.

A device for optically measuring a test substance in blood using the nail as an optical window according to the present invention comprises an irradiation means which applies light within a wavelength range for measuring the absorbance by a test substance to the nail of a subject, a detection means which detects light diffused/reflected from or transmitted through the body of the subject, and a processing means which processes a signal obtained by the detection means and converts it to the concentration of the test substance.

Figure 10:
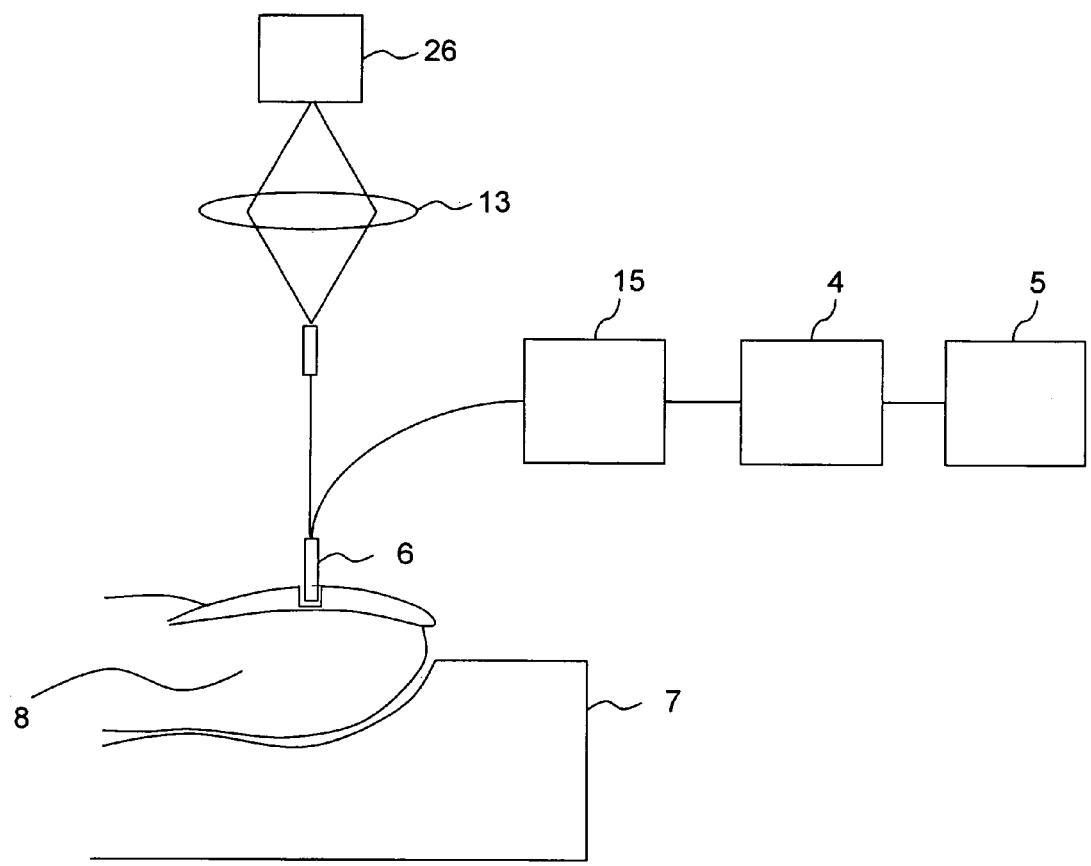
FIG. 10 is an example of a device for measuring a blood substance in the nail bed portion.

FIG. 10 shows a schematic view of a device for optically measuring a test substance in blood of the nail bed portion using the nail as an optical window, according to the present invention. When the device of FIG. 10 is used, the nail having a hole formed by evaporation is measured; however, the nail may be measured without being evaporated.

The irradiation means at least has a light source 26 (light-emitting means) and a means guiding light to the nail portion, for example, a light transmitting fiber, and a light converging optical system 13 such as a lens. On the tip portion of the means guiding light to the nail portion, a light irradiation means is provided. Light is applied toward the nail portion from the light irradiation means. The light source 26 is a light emitting unit emitting light having a requisite wavelength. For example, a white light source such as a tungsten lamp, a light emitting diode, and a laser generation unit such as a semiconductor laser may be used. In this case, light having a desired wavelength may be obtained by separating it by a spectrometer. For example, when near infrared light is desired as irradiation light, an IR spectrometer or the like may be used. As the means guiding light to the nail portion, an optical fiber (quartz fiber) may be mentioned. The optical fiber is connected to a light emitting unit at one end and applies light to the nail portion at the other end. The portion for applying light to the nail portion may be in contact or non-contact with the nail portion. Furthermore, the irradiation means may have a filter for separating light and a lens for converging light.

The detection means at least has a light detecting unit 4 detecting light and a means guiding light coming out from a subject to the detecting unit. The light detecting unit 4 detecting light is not limited as long as it has a light sensor function. For example, a photo-diode, Fourier transformation infrared spectrometer (FTIR) and the like may be used. As the means guiding light to the detecting unit, an optical fiber (quartz fiber) may be mentioned. The optical fiber is connected to the light detecting unit at one end and receives light from a subject at the other end. Furthermore, a spectrometer 15 may be arranged upstream of the light detecting unit 4.

The light irradiation means applying the light generated toward the nail portion and the light receiving means receiving reflected/scattered light may integrally form the probe 6.

When light, which is applied to the nail portion and transmitted through the body of a subject, is detected, the portion of the detection means receiving light and the portion of the light irradiation means applying light are preferably positioned at opposite sides of a subject's finger so as to face each other. Furthermore, when light, which is applied to the nail portion, reflected by the body of a subject and again comes out from the nail portion, is detected, the detection means and the light irradiation means are positioned at the same side.

The processing means, which processes a signal obtained by the detection means to convert it to the concentration of a test substance, comprises a processing unit 5 computationally obtaining the concentration of a test substance from data of light detected by the detection means, such as intensity and wavelength data. The processing unit 5 comprises a memory, in which a signal from the light detection means is stored, a central processing unit (CPU) which processes the signal from the light detection means, and a memory unit such as a hard disk, in which conditions and parameters required for processing in the CPU such as a calibration curb or a calibration equation (described later) and processed results are stored. The processing unit may have a data display section having a monitor for displaying data and a printer.

Furthermore, the device of the present invention may comprise a monitoring means monitoring the water content and keratin content in the nail by using light within a wavelength range for measuring absorption by water in the nail and light within a wavelength range for measuring absorption by keratin in the nail.

The monitoring means (monitoring the water content and keratin content in the nail using light within a wavelength range for measuring absorption by water in the nail and light within a wavelength range for measuring absorption by keratin in the nail) may comprise an irradiation means applying light beams having wavelengths for monitoring keratin and water, and a detection means detecting light diffused and reflected from the nail plate portion. The irradiation means has at least a light emitting means and a means guiding light to the nail portion. The detection means has at least a detecting unit detecting light and a means guiding light coming out of a subject to the detecting unit. The light emitting means, the means guiding light and the detecting unit are the same as described above.

The concentration of a test substance is calculated using a calibration curve or a calibration equation. The calibration curve or calibration equation can be previously obtained by analyzing absorption spectra of a single or a plurality of persons obtained in various conditions. The analysis may be performed by regression analysis such as multiple regression analysis, main component analysis and PLS method.

Furthermore, the device of the present invention may comprise an irradiation means applying light generated from a coherent light source to the nail plate for partly removing the nail plate by evaporating the nail plate by irradiation of laser light, and may further comprise a light detection means detecting fluorescence emitted from the nail plate and the dermis for monitoring the evaporation depth of the nail plate.

Figure 8:
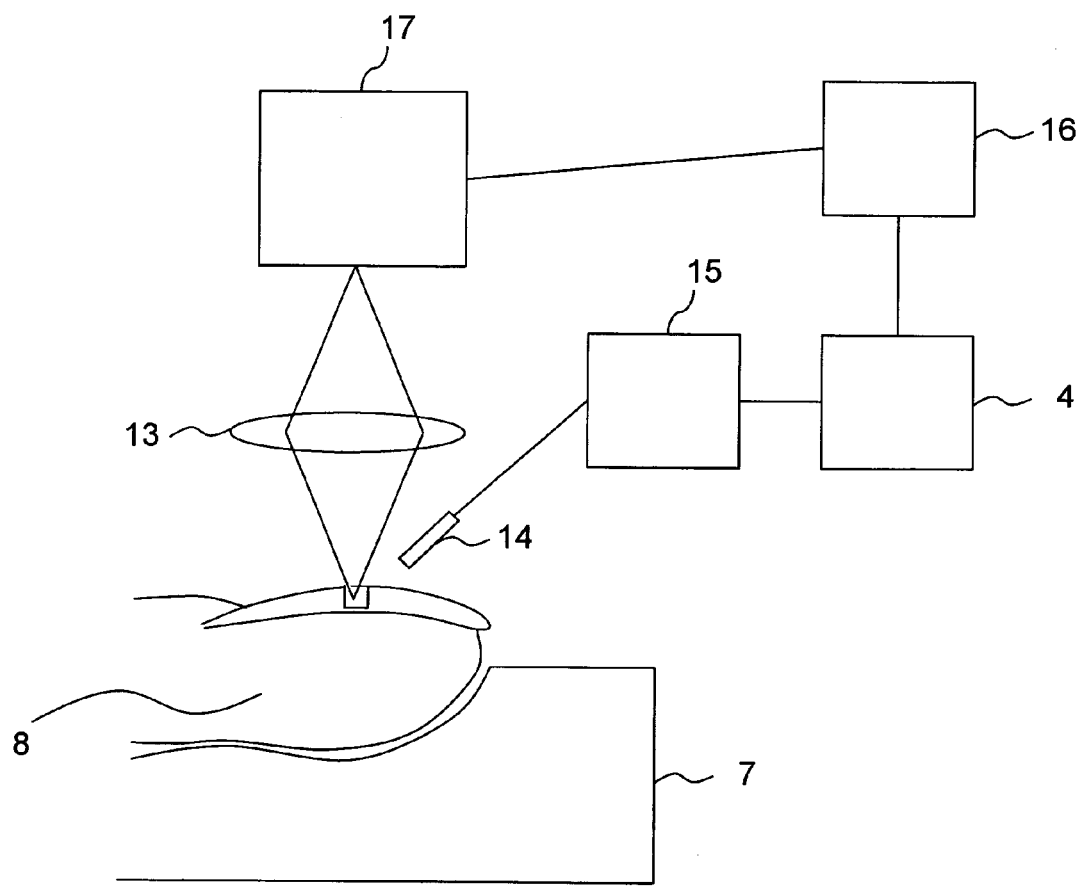
FIG. 8 is a evaporation device for forming a hole in the nail plate.

Moreover, a evaporation device, itself, which comprises these two means for forming a hole in the nail plate, may be encompassed in the present invention. FIG. 8 shows an example of the evaporation device. As shown in FIG. 8, the evaporation device comprises a coherent light source 17, a light converging optical system 13 converging light from the light source to the nail plate, a light receiving means 14 for receiving fluorescence emitted from the nail plate and the dermis, a spectrometer 15 separating the received light, a light detecting unit 4 for detecting light separated by the spectrometer, and a control unit 16 controlling timing of light irradiation from the light source and light detection by the light detecting unit. The light irradiation means (applying light toward the nail portion) and the light receiving means receiving reflected/scattered light may integrally constitute a probe.

Figure 9:
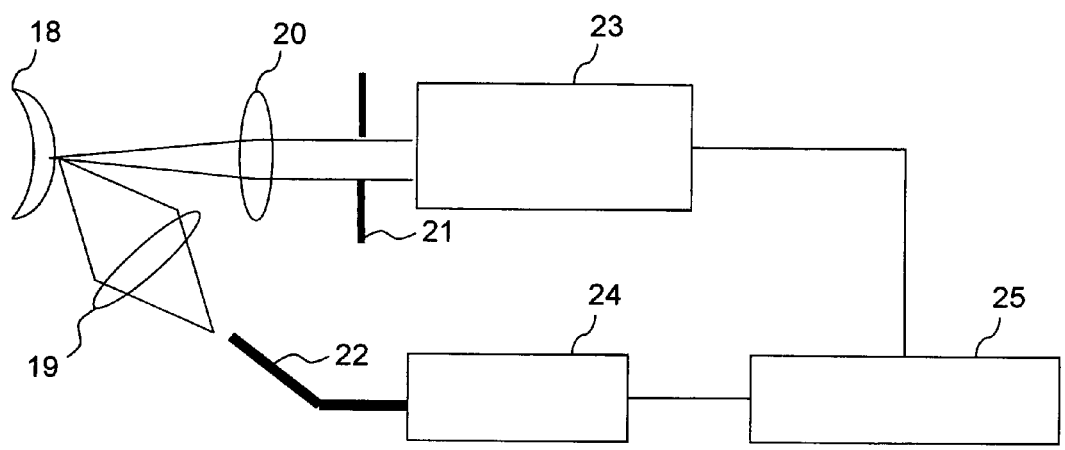
FIG. 9 is a specific example of the evaporation device for the nail plate.

FIG. 9 shows a specific embodiment of the evaporation device. According to the embodiment shown in FIG. 9, an excimer laser 23 is used as a coherent light source, and a CCD spectrometer 24, which comprises a diffraction grating spectrometer and a CCD light detector integrally into a one body, is used as the spectrometer and the light detecting unit, and a pulse generator 25 is used as a controlling unit. FIG. 10 shows an example of a device measuring a blood substance in the nail bed. As is shown in FIG. 10, the device measuring a blood substance in the nail bed comprises a light source 26, a light conversing optical system 13, a probe applying light to the nail and receiving light transmitted through or diffused/reflected from the nail bed, a spectrometer 15 separating the received light, a light detecting unit 4 for detecting light separated by the spectrometer, and a processing unit 5 processing a glucose concentration based on the signal obtained by the light detecting unit.

Furthermore, the device of the present invention may have an immobilizing/holding means for immobilizing a finger. The holding means may be an immobilizing table 7 as shown in FIG. 10 or may have a ring form structure for inserting a finger. The immobilizing/holding means may have an irradiation means and a detection means and/or a means for applying light from a coherent light source for evaporation and a fluorescent detection means for monitoring a evaporation depth.

The device for measuring a blood substance through the nail and the evaporation device according to the present invention may be non-integrally provided. In this case, first a hole is formed in the nail plate by the evaporation device and then a blood substance of the nail bed portion is measured by the measuring device. Alternatively, the device for measuring a blood substance through the nail and the evaporation device may be integrally provided. In this case, a light source for measurement, a light source for nail-plate evaporation, a measuring means, and a means for monitoring a evaporation depth are integrally contained in a single device.

Furthermore, the present invention is directed to a method controlling a device, which is used for optically measuring a test substance in blood using the nail as an optical window and which comprises an irradiation means applying light within a wavelength range for measuring absorption by the test substance to the nail of a subject, a detection means detecting light diffused/reflected from or transmitted through the body of the subject, and a processing means processing signal obtained by the detection means to convert the signal the concentration of the test substance. This is a method of controlling a measurement device, that is, a method of controlling a device for optically measuring a test substance in blood using the nail as an optical window, comprising a step of applying light by controlling an irradiation means applying light within a wavelength range for measuring absorption by the test substance to the nail of a subject, a step of detecting light diffused/reflected from or transmitted through the body of the subject by controlling a detection means detecting light diffused/reflected from or transmitted through the body of the subject, and a step of processing a signal detected to convert the signal the concentration of the test substance. In this case, the control of the light irradiation means includes controlling wavelength and intensity of the light to be applied by the light emitting unit. The control of the detection means includes controlling the detecting unit so as to obtain an absorption spectrum or controlling the detecting unit so as to detect light having a predetermined wavelength alone.

The present invention encompasses a method of controlling a monitor means monitoring the water content and keratin content of the nail by use of light within a wavelength range for measuring absorption by water in the nail and light within a wavelength range for measuring absorption by keratin in the nail. This method comprises a step of applying light within a wavelength range for measuring absorption by water in the nail and light within a wavelength range for measuring absorption by keratin in the nail, a step of detecting light diffused/reflected from or transmitted through the body of a subject by controlling a detection means detecting light diffused/reflected from or transmitted through the body of a subject, and a step of monitoring a water content and keratin content in the nail plate by controlling a processing means of a detected signal. Furthermore, this method comprises a step of accurately obtaining the concentration of a blood substance by correcting a measurement value of the blood substance by a value in accordance with optical characteristics of the nail plate. This step is performed by controlling two devices in combination with a controlling method for a device, which optically measures a test substance in blood using the nail as an optical window and which comprises an irradiation means applying light within a wavelength range for measuring absorption by the test substance to the nail of a subject, a detection means detecting light diffused/reflected from or transmitted through the body of the subject, and a processing means processing a signal obtained by the detection means to convert the signal the concentration of the test substance.

Moreover, the present invention encompasses a method of controlling a device, which partly removes the nail plate by evaporating it by applying light generated from a coherent light source to the nail plate in order to optically measuring a test substance in blood in the nail bed portion using the nail as an optical window, and which comprises an irradiation means applying light generated from a coherent light source to the nail plate and a evaporation-depth monitoring means having a light detection means detecting fluorescence emitted from the nail plate and the dermis for monitoring the evaporation depth of the nail plate. The method comprises a step of applying light generated from a coherent light source to the nail plate under appropriate irradiation conditions by controlling an irradiation means applying light generated from a coherent light source to the nail plate, and a step of monitoring a evaporation depth of the nail plate by controlling a light detection means for detecting fluorescence emitted from the nail plate and the dermis. Furthermore, this method comprises a step of accurately obtaining the concentration of a blood substance by controlling two devices in combination with a controlling method for a device, which optically measures a test substance in blood using the nail as an optical window and which comprises an irradiation means applying light within a wavelength range for measuring absorption by the test substance to the nail of a subject, a detection means detecting light diffused/reflected from or transmitted through the body of the subject, and a processing means processing a signal obtained by the detection means to convert the signal the concentration of the test substance.

EXAMPLES

The present invention will be described by way of the following Examples; however, which should not be construed as limiting the invention.

Example 1

Estimation of Sensitivity of Measurement System for Blood Glucose Level in the Nail Bed Portion (1) Calculation of Density of Capillary Vessel Under the Nail To prove that the capillary vessel exists in a high density in the nail bed portion and quantify a glucose level in the nail bed tissue, an image of the capillary vessel in the nail bed portion shown in a document was processed by Adobe Photoshop to computationally obtain the area of the image occupied by capillary vessel.

The capillary vessel was traced from the image of the portion under the nail shown in FIG. 2 (Hasegawa K., J. Hand Surgery, Vol. 26A, No. 2, pp 283-90, 2001) to calculate the areas of the vessel and the other region. The calculation was performed with respect to three points to obtain an average. The area ratio of the capillary vessel of the portion under the nail was 44%. According to another document (Pasyk K. A., Plastic and Reconstructive Surgery, Vol. 83, No. 6, pp. 939-947, 1989), the density of the capillary vessel is about 3% in the upper arm and about 7% in the palm. From this, the density of the capillary vessel in the portion under the nail is said to be extremely large.

(2) Selection of Wavelength for Glucose Measurement

To confirm that light absorption by glucose is localized in the near infrared region, transmitted light was measured by a Fourier-transform infrared spectrometer, FTIR-620 (JASCO Corporation, Tokyo). Then, investigation was made on the wavelength absorbed by glucose and absorbance of glucose.

Figure 11:
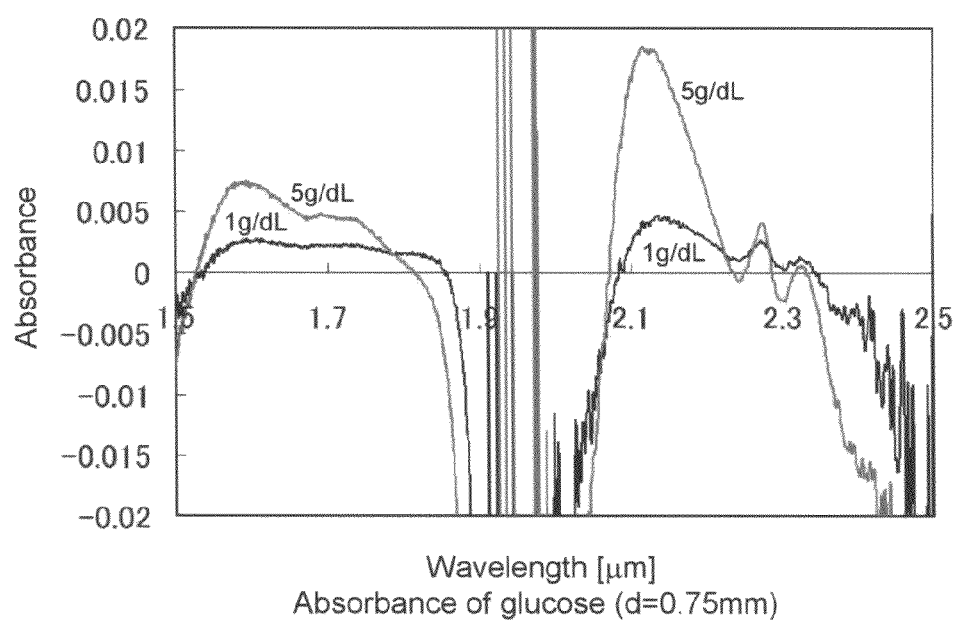
FIG. 11 is an absorption spectrum of glucose.

Aqueous glucose solutions (concentration: 1 g/dl and 5 g/dl) were prepared. The light transmitted through the solutions having a solution thickness (depth) of d=0.75 mm was measured. The absorbance of glucose was calculated by subtracting the absorbance of water, which was measured through an aqueous solution having the same thickness, from the value obtained above. FIG. 11 shows an absorption spectrum of glucose and Table 1 shows light absorption peaks of glucose samples.

TABLE 1

Absorption peak of glucose

| peak [μm] | base1 [μm] | base2 [μm] | 5 g/dL glucose Abs. | 1 g/dL glucose Abs. | water Abs | 10 mg/dL glucose Abs./water Abs. |
|---|---|---|---|---|---|---|
| 2.136 | 2.243 |  | 0.0187 | 0.0038 | 0.82 | 4.56E-05 |
| 2.273 | 2.243 | 2.303 | 0.0057 | 0.0018 | 0.75 | 1.52E-05 |

When the peaks emerging at a wavelength of 2.136 μm and 2.273 μm are compared, the ratio of glucose absorbance obtained at a wavelength of 2.136 μm relative to that of water obtained at the same wavelength is approximately three-fold as high as that obtained at the other wavelength. From this, it is estimated that the quantification of glucose can be performed more accurately by use of the wavelength of 2.136 μm.

(3) Controlling the Concentration of a Latex Beads Solution for Simulating the Skin Scattering To perform an experiment of glucose measurement by measuring diffused/reflected light from the capillary vessel in the nail bed portion using a model, the model was prepared by using a latex beads solution whose concentration was determined so as to simulate the scattering characteristics of the skin.

The isotropic scattering coefficient and anisotropic scattering parameter of the skin were checked in documents and the concentration of an aqueous solution of beads having diameters of 1.5 μm was determined so as to approximately match with the isotropic scattering coefficient of the skin by means of the Mie scattering calculation software (Oregon Medical Laser Center; http://omlc.ogi.edu/calc/mie_calc.html).

The optical characteristics of the skin (Troy T. L., J. Biomedical Optics, 6(2), pp. 167-76, 2001) were as follows.

The scattering coefficient of the skin shown in documents (near 2.1 μm): $\mu_s'=10\pm2.3$ cm$^{-1}$ Non anisotropic scattering parameter of the skin: g=0.85.

The concentration of a latex bead solution was determined in accordance with Mie scattering theory, as follows.

Individual Parameters

Latex (polystyrene) index of refraction: $n_p$=1.525 ($\lambda$=2.5 μm) (Larena. A, Spectroscopy letters, Vol. 25, No. 4, pp. 447-461, 1992)

Latex density: 1.055 g/cm$^3$

Index of refraction of water: $n_w$=1.30 ($\lambda$=2.0 μm) (Hale G., Appl. Opt., Vol. 12, No. 3, pp. 555-563)

Figure 12:
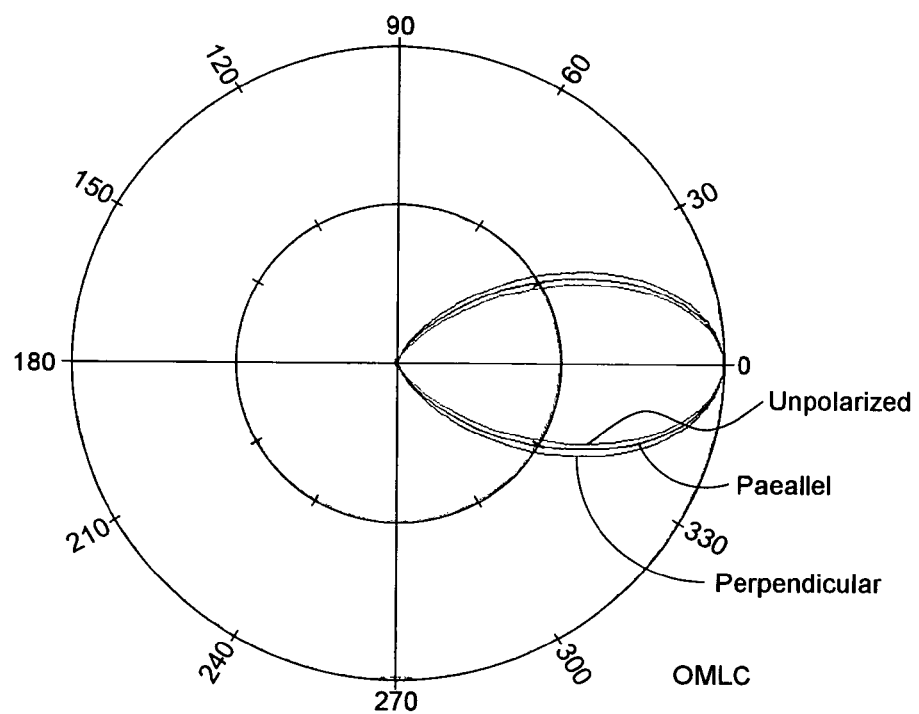
FIG. 12 shows a Mie scattering pattern of latex beads.
Figure 13:
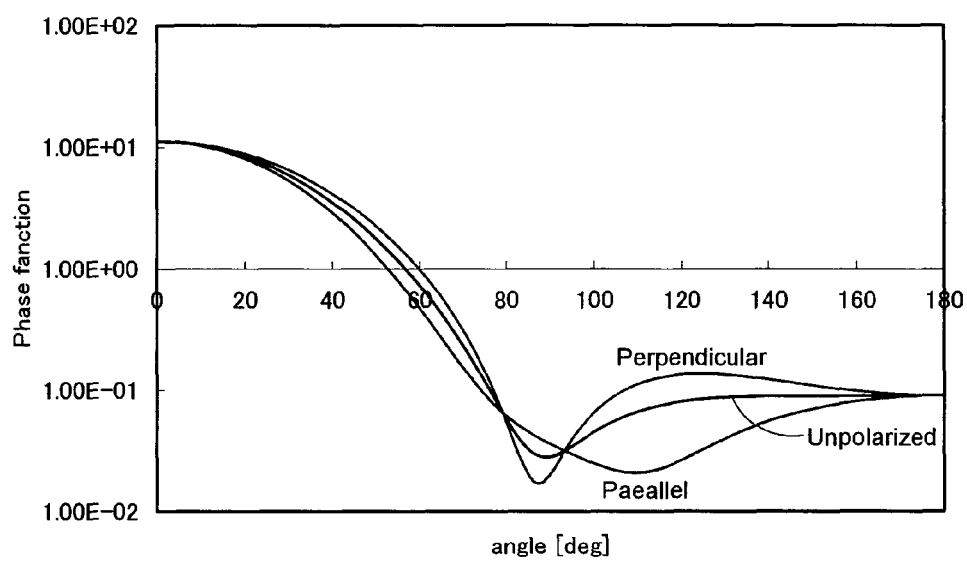
FIG. 13 shows $P(\theta)$ of latex beads.

As a result of calculation, a skin scattering simulation model was a latex beads solution containing particles of 1.53 μm in diameter in a density of 0.0055 particles/(μm)$^3$ and having $\mu_s'$=11.0 cm$^{-1}$ and g=0.78 at a concentration of the latex beads solution of 1.1%. FIG. 12 shows Mie scattering pattern of latex beads ($\phi$1.53 μm) at a wavelength of 2.1 μm. FIG. 13 shows P($\theta$) of the latex beads ($\phi$1.53 μm) in water at a wavelength of 2.1 μm.

For reference, the calculation results of Mie scattering are shown below.

<Input Parameters>
The diameter is 1.53 microns
The wavelength is 2.1 microns
The real index of refraction is 1.53
The imag index of refraction is 0
The number of angles is 91
The density of scatterers is 0.0055 per cubic micron.
<Calculated Coefficients>
The size parameter (x) is 2.98
The extinction efficiency (Qext) is 0.501
The scattering efficiency (Qsca) is 0.501
The absorption efficiency (Qabs) is $-1.11e^{-16}$
The backscatter efficiency (Qback) is 0.0408
The geometric cross section is 1.84 μm
The total extinction coefficient is 5.06 mm$^{-1}$ (50.6 cm$^{-1}$)
The scattering coefficient is 5.06 mm$^{-1}$ (50.6 cm$^{-1}$)
The reduced scattering coefficient is 1.10308 mm$^{-1}$ (11.0308 cm$^{-1}$)
The absorption coefficient is $-1.12e^{-15}$ mm$^{-1}$ ($-1.12e^{-14}$ cm$^{-1}$)
The anisotropy is 0.782

(4) Glucose Measurement by Microscopic FTIR Based on Reflected Light

To estimate the feasibility of measuring glucose in the nail bed portion and the requisite accuracy of the measurement system, diffused/reflected light of a solution model was measured by FTIR.

Figure 14:
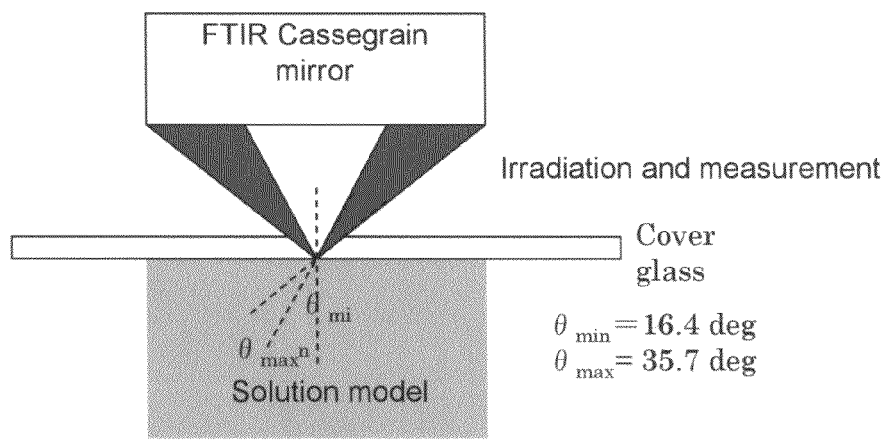
FIG. 14 is a view showing a measurement system for light reflected from a solution model by microscopic FITR.

As shown in FIG. 14, reflected light from a 1.1% latex beads solution simulating scattering of the skin was measured by microscopic FTIR. The same measurement was performed using pure water instead of the solution. The obtained value was regarded as a mirror surface reflectivity. The mirror surface reflectivity was subtracted from the reflectivity of the latex beads solution to obtain a diffusion reflectivity. The background of each measurement was obtained based on aluminum total reflectivity.

Figure 15:
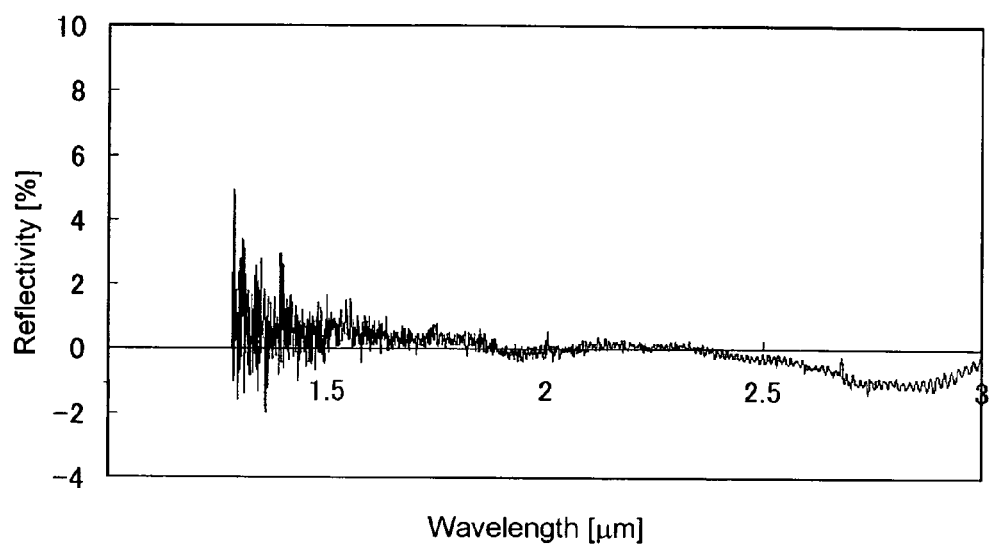
FIG. 15 is a graph showing a diffusion reflectivity of a latex beads solution simulating scattering by the skin.

FIG. 15 shows the diffusion reflectivity of the latex beads solution simulating scattering of the skin. As shown in FIG. 14, the diffusion reflectivity of the solution model in the near infrared region was substantially 0%. In the Monte Carlo simulation using optical characteristics of the skin, the total diffusion reflectivity resulted in 1.2%. These values are in the same order of magnitude even if a converging efficiency of 0.26 is taken into consideration. Furthermore, a slight peak is observed at near a wavelength of 1.935 μm, which corresponds to absorption by water. From the above, it is considered that a diffused/reflected light was captured; however, the amount of diffused/reflected light from the latex beads solution (simulating scattering of the skin) was not measured with a sufficient S/N ratio for detecting glucose signal by the microscopic FTIR used in measurement.

Next, to estimate which degree of sensitivity is required for a calculation system, measurement was performed by using alumina, which was a strong scattering material to increase diffused/reflected light.

Figure 16:
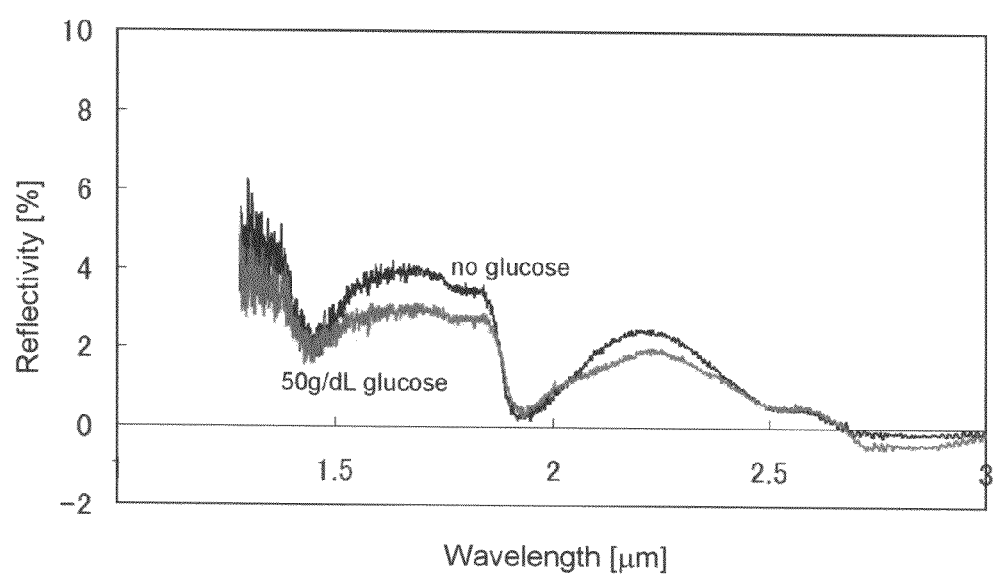
FIG. 16 is a graph showing a diffusion reflectivity of a 50% alumina solution.

A reflected light was measured by microscopic FTIR with respect to an aqueous solution model containing 50% $Al_2O_3$ and a 50 g/dl glucose. A diffusion reflectivity was calculated in the same manner as in the latex beads solution. FIG. 16 shows the diffusion reflectivity of the 50% alumina solution.

Figure 17:
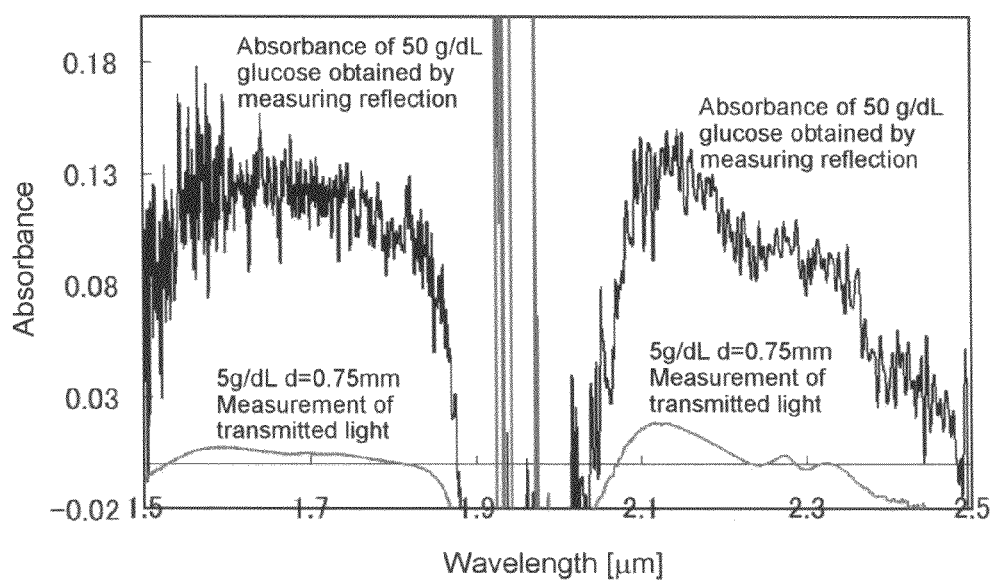
FIG. 17 is spectrum showing an absorption spectrum of glucose of a solution containing 50% alumina and 50 g/dl glucose.

The diffusion reflectivity was converted in terms of absorbance to obtain the absorbance of glucose. FIG. 17 shows the absorbance of glucose. The peak was consistent with that of the glucose absorption spectrum obtained based on transmission. In this case, the S/N value was 2.3 (at the peak at a wavelength of 2.1 μm).

(5) Investigation on Improvement of S/N Value for Attaining Glucose Measurement in Capillary Vessel Under the Nail Based on the results of Example, investigation was made on measurement of glucose in the capillary vessel under the nail.

Figure 18:
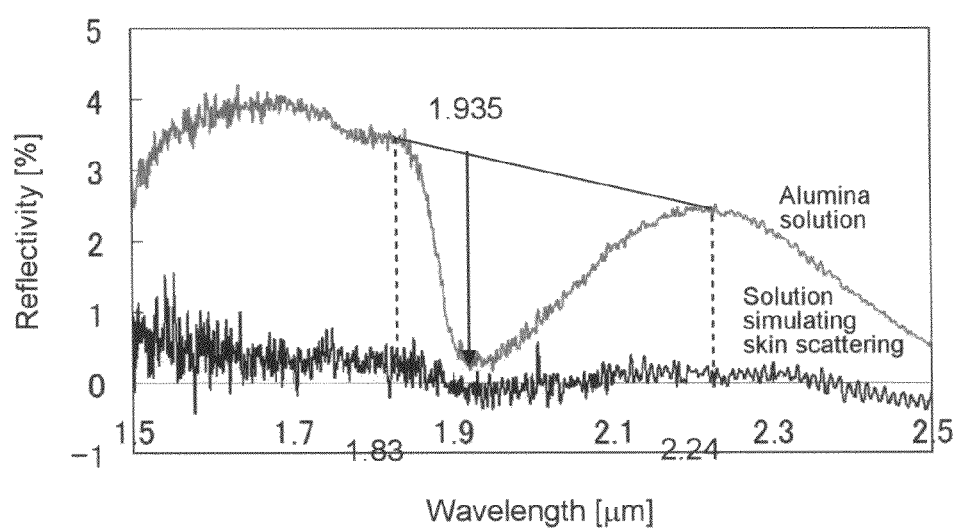
FIG. 18 is a graph showing absorbance of water in a solution simulating a scattering by the skin in comparison with that of an alumina solution.

First, the ratio of a glucose light absorption signal in the diffused/reflected light from the capillary vessel under the nail actually measured was estimated. Assuming that the light absorbing materials existing in the tissue were only water and glucose, as the simplest case, the absorbance ratio of water to glucose depends upon only the concentration of glucose, even though the optical path differs in the tissue. Then, based on the absorbance of water (peak: 1.935 μm, base line: 2.24 μm, 1.83 μm) in light diffused/reflected from a latex beads solution simulating scattering of the skin and an alumina solution, the S/N ratio was estimated when glucose was measured in the latex beads solution simulating scattering of the skin. FIG. 18 shows the results of absorbance values of water in solution models for comparison.

$$2.3 \times \frac{0.053}{0.42} = 0.29$$

This is the result when a glucose level was 50 g/dL. At a desired glucose level (normal glucose) of 100 mg/dL, the following formula was obtained.

$$0.29 \times \frac{100}{50000} = 5.8 \times 10^{-4}$$

Furthermore, since the area ratio of the capillary vessel under the nail is 0.44 as described in Example 1, the absorbance of glucose is:

$$5.8 \times 10^{-4} \times 0.44 = 2.6 \times 10^{-4}$$

Therefore, to measure glucose of 100 mg/dL with an S/N ratio=1, it was found that S/N ratio is required to improve by $3.8 \times 10^3$.

To improve the S/N ratio, investigation was made on the FTIR measurement system presently in use. Noise is primarily caused by FTIR itself. To improve the S/N ratio, two approaches may be considered. One is to increase signal intensity and the other is to reduce noise. Investigation was made on each of them.

To increase signal intensity, roughly two approaches are considered. One is to increase a light converging efficiency and the other is to increase the amount of incident light. First, the converging efficiency was investigated.

As shown in FIG. 14, light is converged by a Cassegrain mirror in the FTIR system. The viewing angle thereof is limited to 16.4 to 35.7°.

Figure 19:
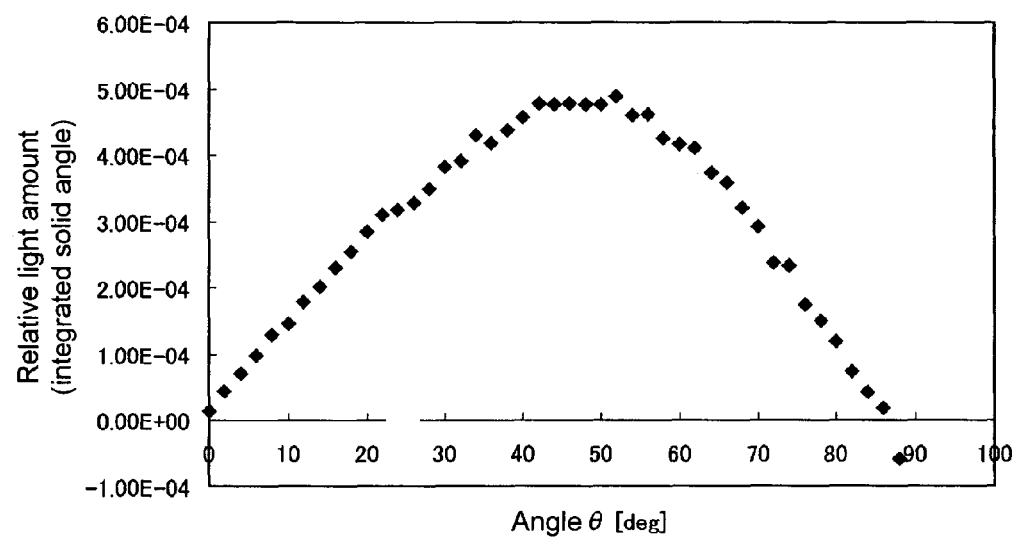
FIG. 19 is a graph showing dependency of diffused/reflected light upon an angle in a solution simulating scattering by the skin.

The dependency of diffused/reflected light upon the angle was simulated in accordance with the Monte Carlo simulation (Oregon Medical Laser Center, http://omlc.ogi.edu/software/mc/index.html) and the light converging efficiency of FTIR was computationally obtained. The results are shown in FIG. 19. When the ratio of an integrated value of the viewing angle relative to that of the total angle was obtained from FIG. 19, the light converging efficiency was 0.26. It was therefore found that a 3.8 fold increase in signal intensity can be attained in the approach of improving the light converging efficiency.

Figure 20:
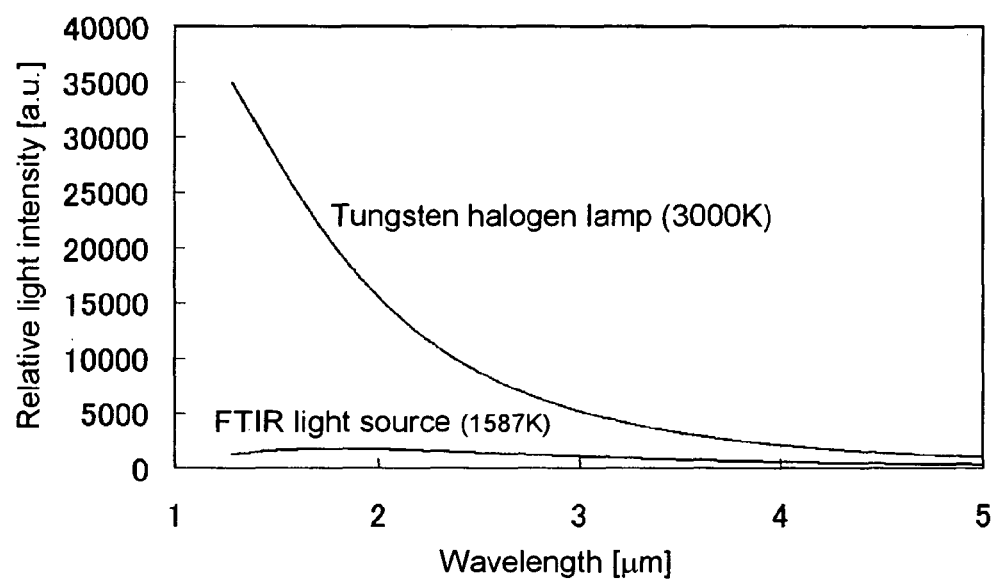
FIG. 20 is a black body radiation spectrum of light sources different in temperature.

Next, investigation was made on the amount of light incident. The FTIR light source is a ceramic light source of 1300° C. and the blackbody radiation spectrum thereof is as shown in FIG. 20. The overall output of light incident upon a sample chamber was measured by a thermopile. It was 74 mW. The output of light at a wavelength of 2.1 μm was calculated based on a relative value at each wavelength. It was $1.5 \times 10^{-2}$ mW (wavelength width: about 0.4 nm). This is converted into the light output of a tungsten halogen lamp of 3000K. The output is 8.1 fold as large as that of the FTIR assuming that both have the same emissivity.

Furthermore, investigation was made on a detector.

Figure 21:
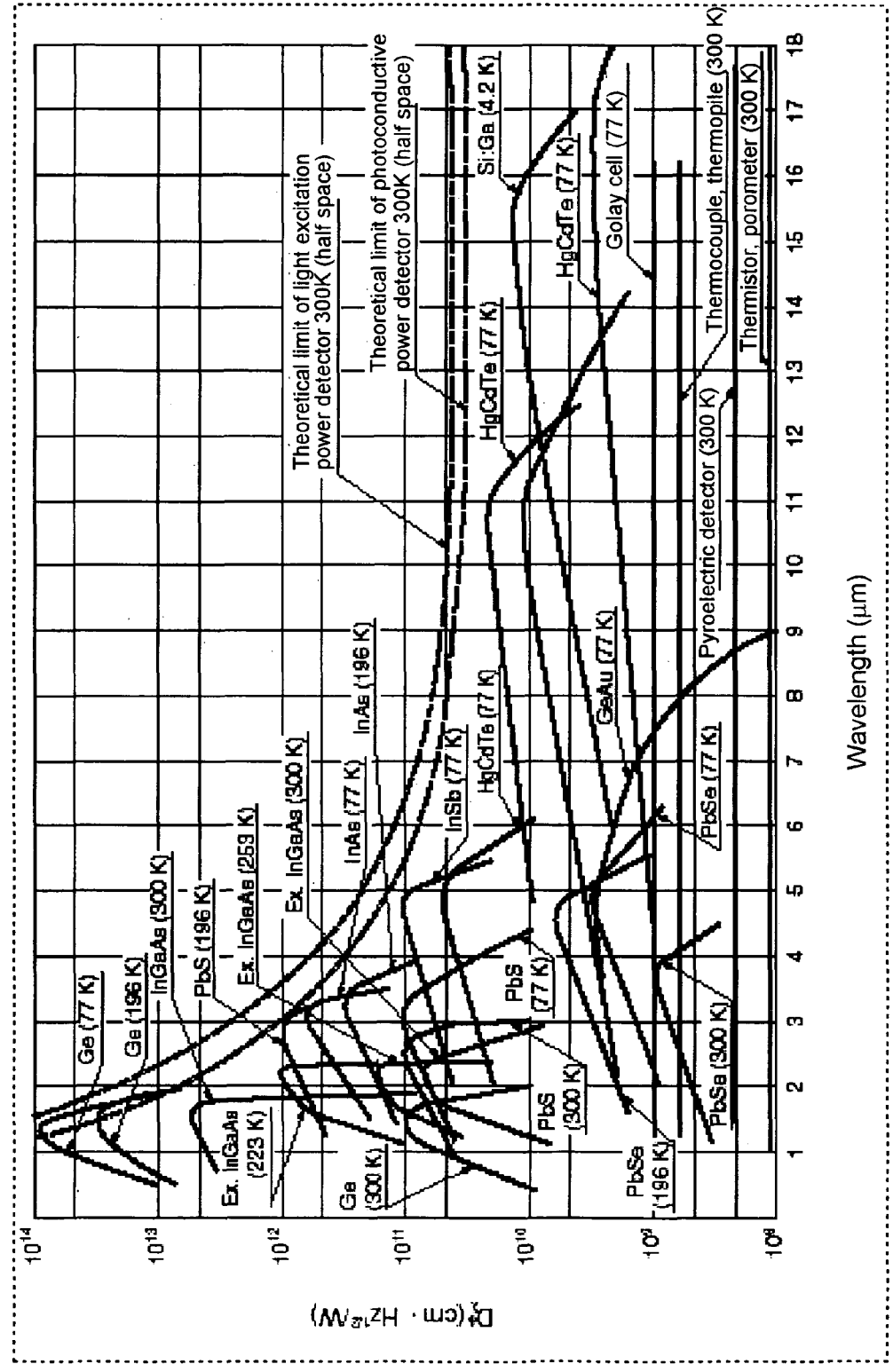
FIG. 21 is a graph showing detection abilities of light detection devices.

The MCT detector presently in use has a wavelength showing a maximum sensitivity at near 10 μm, and a specific detectivity (D*) of about $3 \times 10^8$ at a wavelength of near 2 μm. A PbS device or the like, which have a wavelength showing a maximum sensitivity at near 2.5 μm, has D* of $3 \times 10^{11}$ at near 2 μm. From this, it is simply considered that if the detector is replaced by a detector for infrared light, about a 1000-fold increase of S/N ratio can be expected. In FIG. 21, the detection abilities of light detecting devices are compared (excerpt from the Web site (home page) of Hamamatsu Photonics, K.K.).

To summarize, it is estimated that the S/N ratio is improved to at most $3.08 \times 10^4$, meaning that the measurement accuracy can be improved to at most ±12.3 mg/dL in terms of glucose concentration.

Example 2

Effect of Disturbing Agents Such as Keratin and Water on the Nail Plate
(1) Sample Treatment Nail plate was taken from human individuals (4 individuals). The upper and lower sides (dorsal and ventral sides) of each of the nail plates were polished with sandpaper to prepare 7 samples.

The samples were allowed to stand still for 20 hours in 6 types of environments different in humidity: a humidity of 14% (a saturated aqueous LiCl solution), 48% (a saturated aqueous MgCl solution), 67% (a saturated aqueous NaBr solution), 77% (a saturated aqueous NaCl solution), 85% (a saturated aqueous KCl solution) and 96% (pure water). In this manner, the water contents of the samples were changed. The samples were weighed. An increase from the weight of each sample at a humidity of 0% extrapolated was regarded as a water content.

(2) Measurement of Infrared Transmittance

Figure 22:
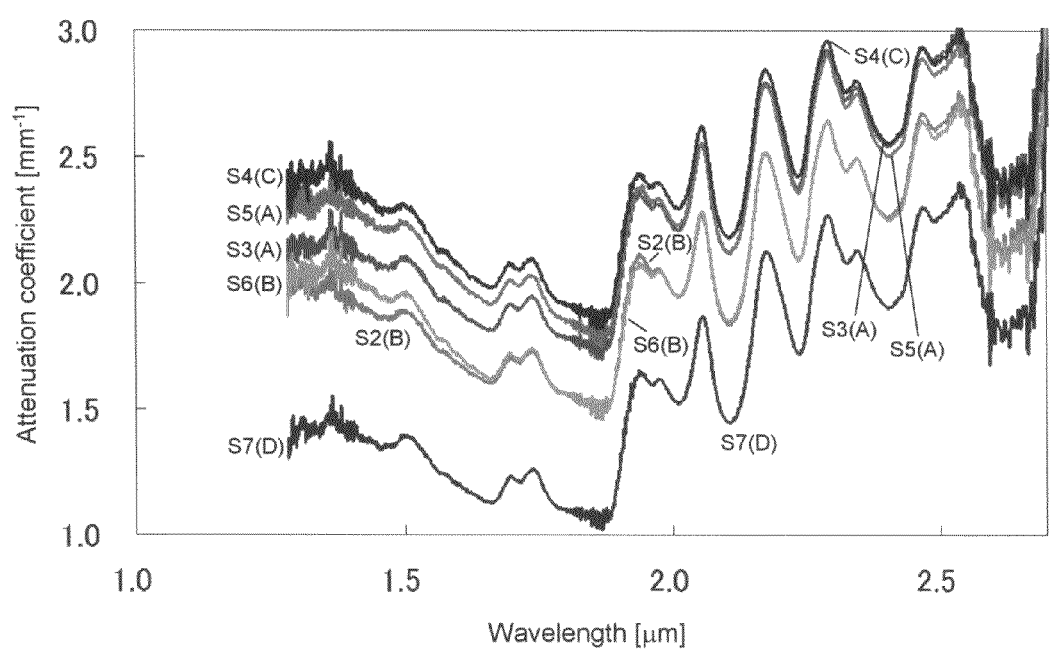
FIG. 22 is a spectrum showing an attenuation coefficient of nail samples allowed to stand still in a humidity of 14%.

As an infrared spectrometer, FTIR-620 manufactured by JASCO Corporation was used. Using an additional microscopic system IRT-30 optical system, the infrared transmittance of each sample was measured. The spectra obtained from 7 samples were converted into attenuation coefficient spectra in accordance with the Lambert-Beer equation. FIG. 22 shows the attenuation coefficient spectra of samples allowed to stand in the environment of a humidity 14%. Since the water content at this humidity was about 2%, it may be considered that the spectra shown in FIG. 22 are virtually equivalent to the spectra of keratin contained in the nail plate. Several peaks are observed, which are peaks of keratin absorption. It is considered that the base line differs because of influence of scattering. When the spectra are compared to each other, there is a large difference in base line between persons. From this, it is considered that there is individual difference in scattering of keratin fibers. Such an individual difference may produce individual difference in light converging efficiency when light is measured by means of e.g., a probe.

Figure 23:
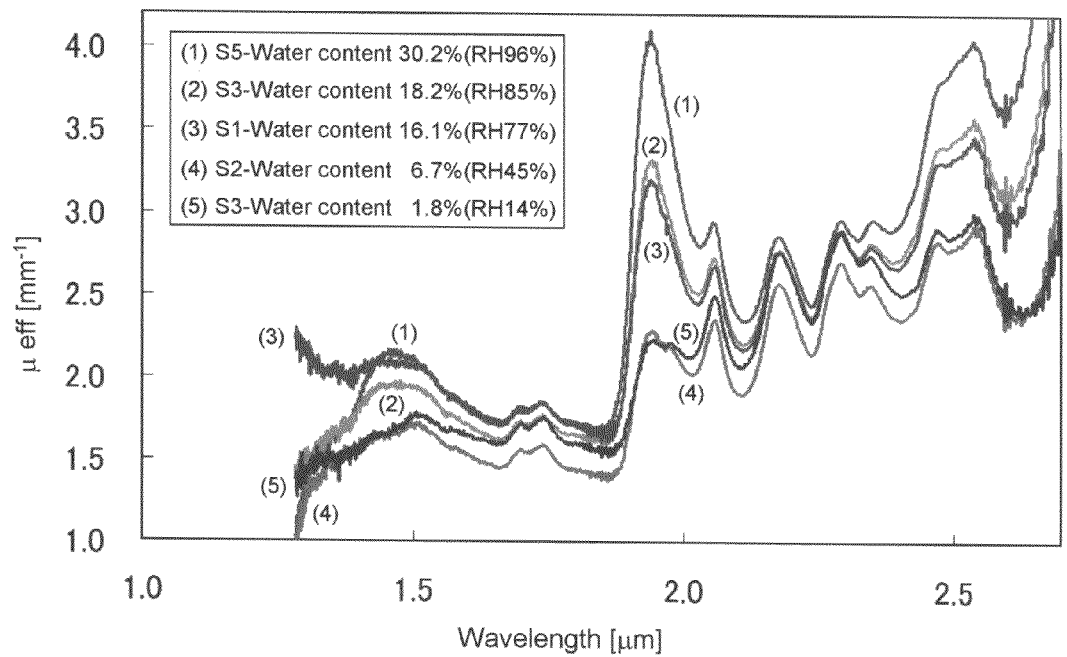
FIG. 23 is a spectrum showing the relationship between the water content of the nail and an attenuation coefficient.

FIG. 23 exemplifies the attenuation coefficient spectra of samples, which were allowed to stand in different environments in humidity. An absorption peak of water emerging at a wavelength of 1.935 μm increases as humidity increases. In accordance with this, the attenuation coefficient increases at a wavelength of near 2.1 μm, at which glucose is measured. In the simulation case where glucose is measured through the nail plate of 0.4 mm thick, water is estimated to be 101 mg/dl per % in terms of noise.

Example 3

Figure 24:
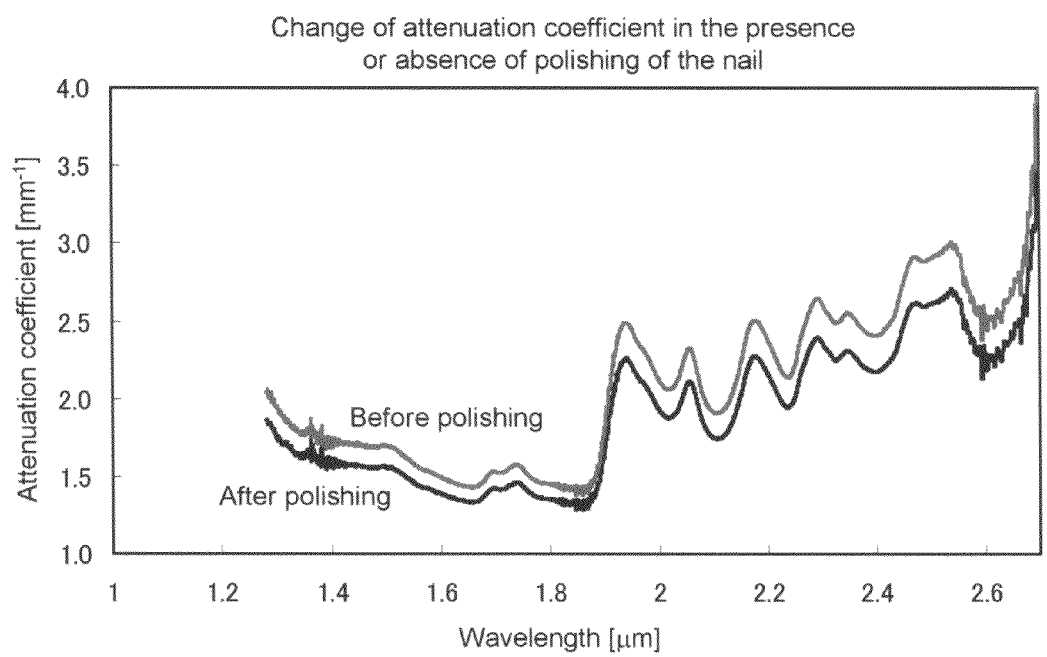
FIG. 24 is a graph showing a change of the attenuation coefficient in the presence or absence of nail polishing.

Investigation on Correction of Disturbance of the Nail Plate (1) Reduction of Scattering by Polishing FIG. 24 shows a change of attenuation coefficient by the presence or absence of polishing of the nail. There are several peaks, which show keratin absorption and water absorption (a wavelength: near 1.9 μm). The base line is influenced primarily by scattering and goes up and down. The sample after polishing shows a lower attenuation coefficient. Since the same sample is used and the profile of the peaks is the same, there is no difference in absorption. The base line is lowered. This is conceivably because scattering from the nail surface is reduced by polishing.

(2) Correction by Keratin and Water Contents Monitored

In the attenuation spectra of the nail plate shown in FIG. 23, the content of keratin per unit optical length can be estimated from the value of one of the absorption peaks present at a wavelength of 2.177 μm, which is within the range of a minimum water absorption. When analysis is made based on the absorption spectrum of keratin within the wavelength range for measuring glucose in combination with the optical length actually used in measurement, light absorption by keratin in the nail plate can be estimated.

Figure 25:
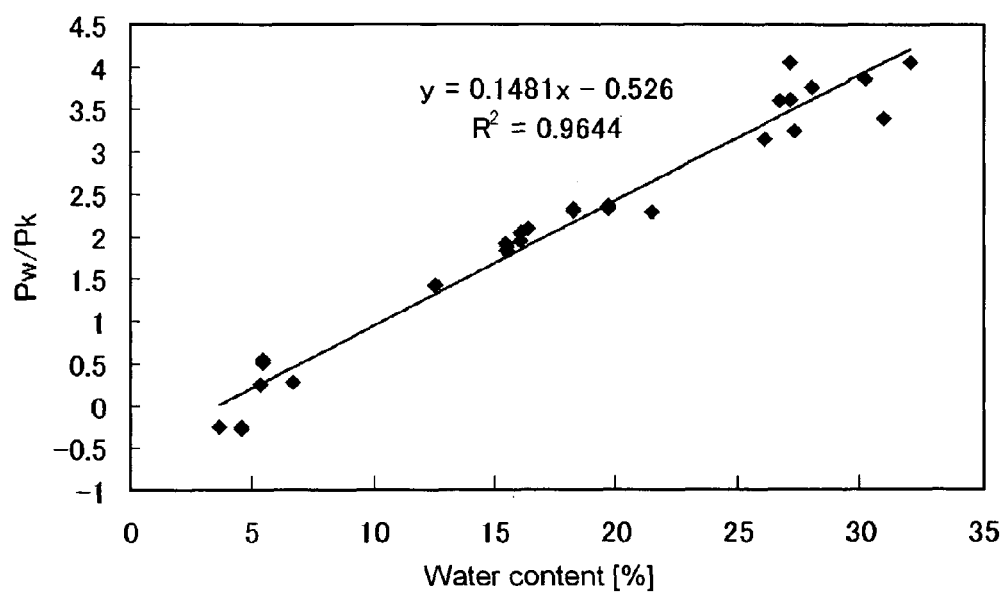
FIG. 25 is a graph showing the relationship between the water content of the nail and $P_w/P_k$.

Using attenuation coefficient at a wavelength of 2.235 μm as a reference value, the ratio of $P_w/P_k$ was plotted in the vertical axis, where $P_w$ is the value of the absorption peak of water at a wavelength of 1.935 μm, and $P_k$ is the value of the absorption peak of keratin at a wavelength of 2.177 μm; on the other hand, the water content (on the weight basis) was plotted correspondingly on the horizontal axis (FIG. 25). As a result, a linear relationship was obtained. The graph shows $R^2=0.9644$ m SEP=1.68% (water content) and thus good correlation was exhibited.

From the results above, the water content of the nail can be estimated. The absorption of light by water in the nail plate can be estimated based on the absorption spectrum of water within wavelength range for measuring glucose in combination with the optical length actually used in measurement. In the simulation case, glucose was measured through the nail plate of 0.4 mm thick and the resultant value was corrected by the absorption of light by water in the nail plate. As a result, a standard deviation was ±85.4 mg/dl. There is a high possibility that a desired value of ±10 mg/dl is obtained by reducing the thickness of the nail plate by scraping it.

Example 4

Evaporation of the Nail Plate for Measuring a Blood Substance Through the Nail Plate (1) Investigation on Optimum Irradiation Conditions for Evaporation of the Nail Plate (1-1) Relationship Between Pulse Energy Density and Evaporation Depth As a coherent light source for evaporating the nail plate, ArF laser C3470 (Hamamatsu Photonics, K.K., Shizuoka) (a wavelength of 193 nm, a pulse width of 15 ns) was used. The nail plate was irradiated by the laser at 2 Hz while changing a pulse energy density within the range of 50 to 1250 mJ/cm²·pulse. Nail plate samples (6 samples in total) used herein were taken from four male persons of twentysomething (A: 3 samples, B-D: single sample).

Generally, it is known that the evaporation depth is given by the following equation
Beer's law blow-off model:

$$E_d = \frac{1}{\mu_a}\text{Ln}\left(\frac{F_0}{F_{th}}\right)$$

$\mu_a$: Absorption coefficient [mm$^{-1}$]
$F_0$: Irradiation fluence [mJ/cm²]
$F_{th}$: Evaporation threshold [mJ/cm²]

Figure 26:
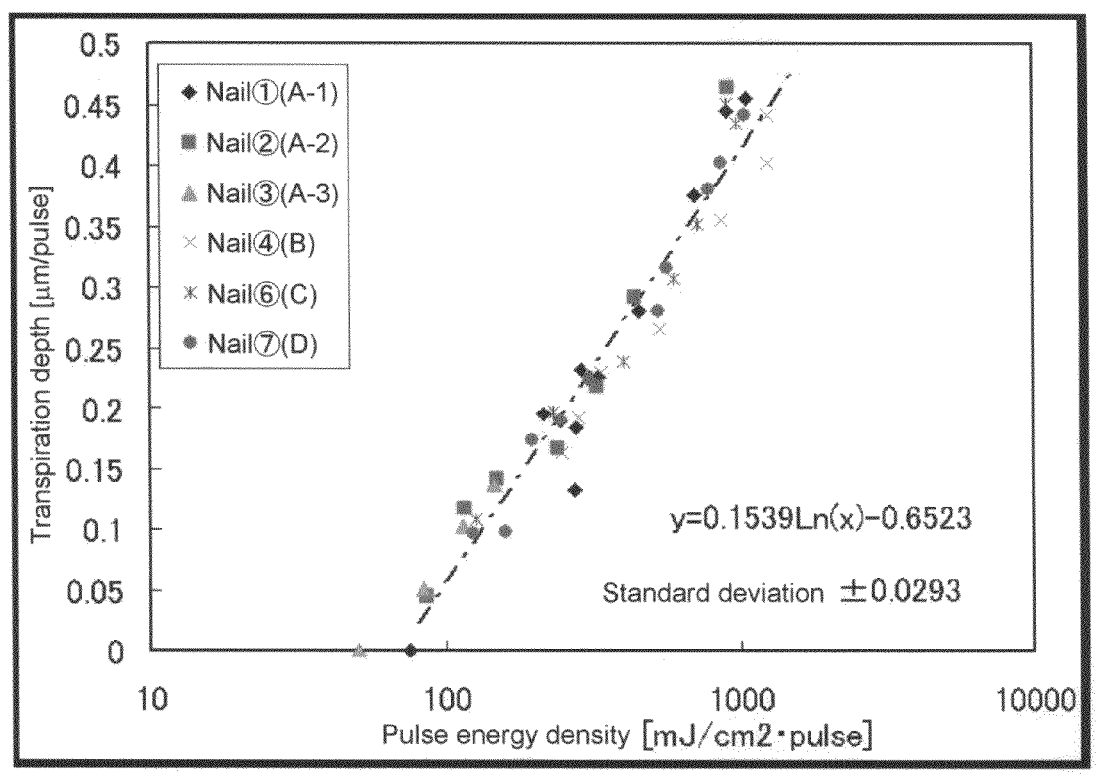
FIG. 26 is a graph showing the relationship between irradiation fluence and evaporation depth in evaporation of the nail plate.

The results are shown in FIG. 26. A logarithmic value of a pulse energy density was plotted on the horizontal axis and a evaporation depth was plotted on the vertical axis. When an approximate curve was drawn in accordance with the aforementioned equation, the relationship was expressed by the equation: y=0.154Ln(x)−0.652. The correlation coefficient was 0.9. Thus, it was confirmed that they have strong correlation. Furthermore, a standard deviation was about ±0.03. From this, it was suggested that the nail plate can be accurately evaporated by use of a laser.

(1-2) Surface Observation of Evaporation Site

The surface of the evaporation site of the nail plate obtained in Section (1-1).

Figure 27:
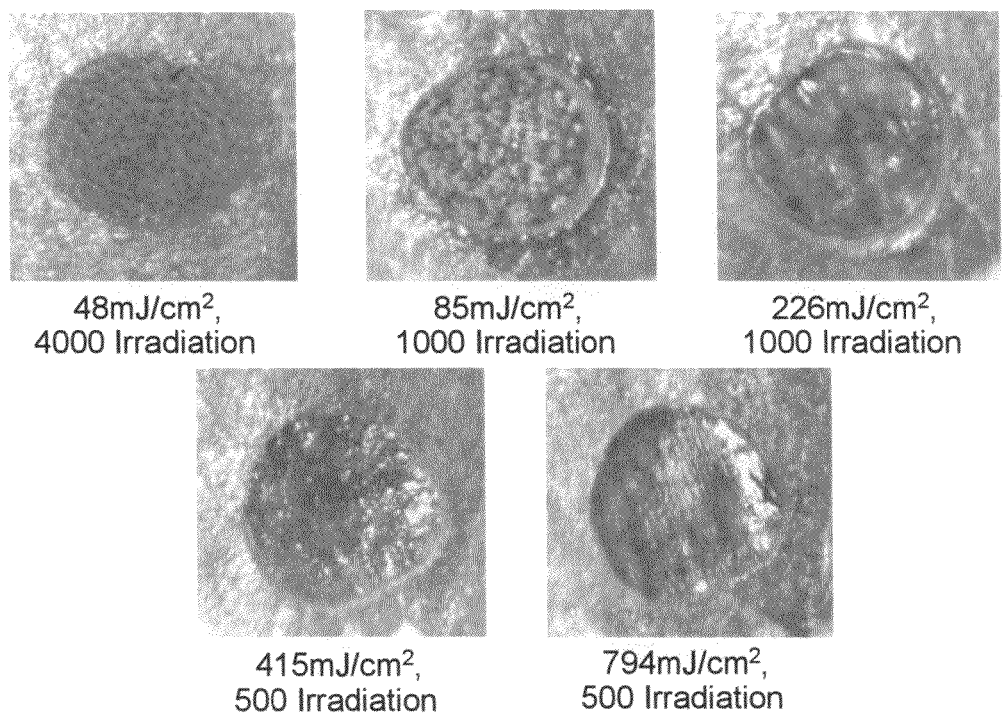
FIG. 27 shows an image (enlarged microscopic image) of the surface of evaporated portion of the nail irradiated with different fluences in evaporation of the nail.
Figure 28:
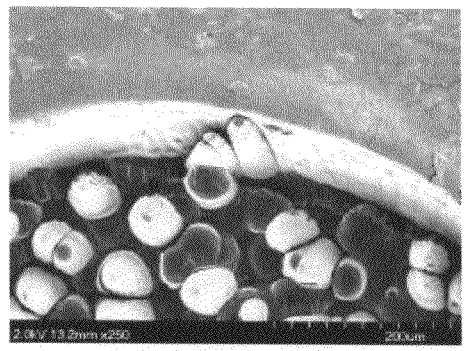
FIG. 28 shows an image (electron microscopic image) of the surface of evaporated portion of the nail irradiated with different fluences in evaporation of the nail.
Figure 28:
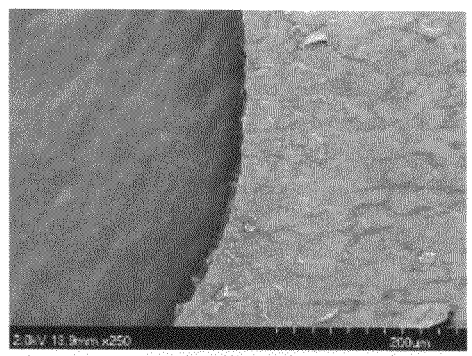
Figure 28:
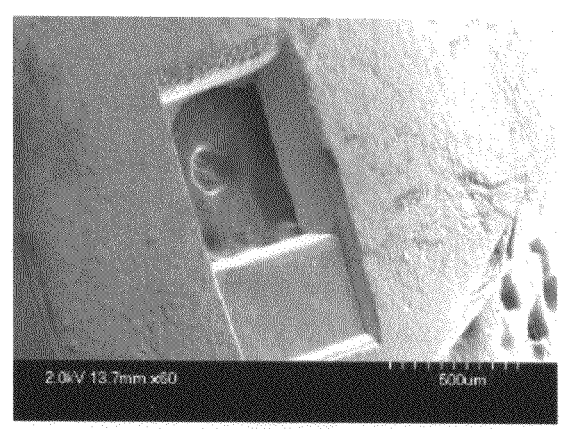

Images of the surface are shown in FIGS. 27 and 28.

When the nail plate was irradiated with a laser of 85 mJ/cm², projections and depressions were observed at the evaporated site.

When the nail plate was irradiated with a laser of 226 mJ/cm² or more, the evaporated site was observed to be flat. This suggests that a flat evaporated surface can be obtained by appropriately selecting a pulse energy density in evaporation.

The evaporated site after evaporation is desirably flat since measurement is optically performed. From this, it was suggested that the nail plate is suitably evaporated by irradiation with a fluence of at least 85 mJ or more.

(2) Investigation on Evaporation Control by Measuring Fluorescence (2-1) Differentiation Between Plume Emission and Fluorescence During evaporation, particles called plume are released in a large amount from a solid body by evaporation and also light is emitted from the plume, which inhibits fluorescence measurement. Thus, first to distinguish plume emission from fluorescence, emission spectra of the nail was measured by applying by light having an irradiation energy density.

Figure 29:
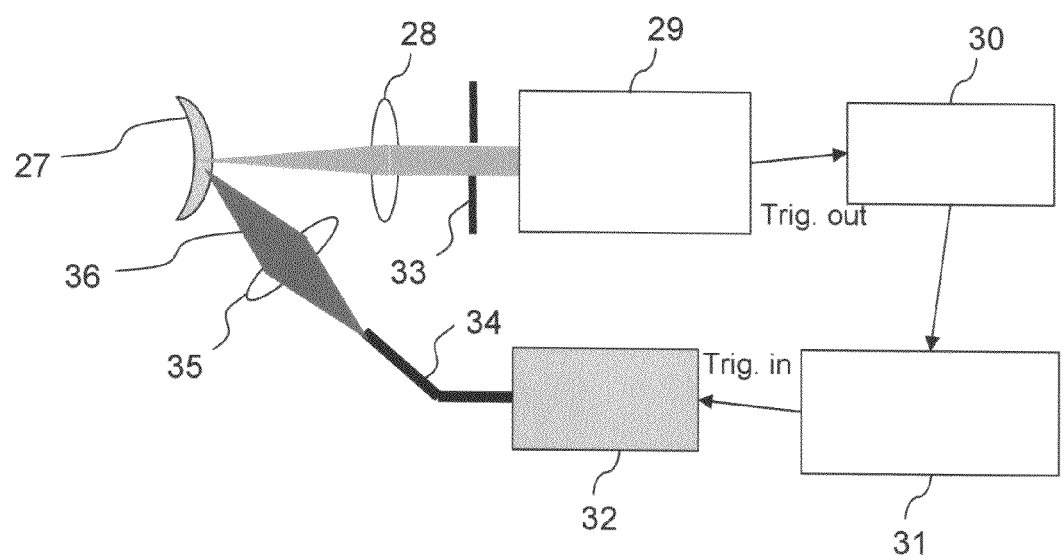
FIG. 29 schematically shows a fluorescence spectrum measurement system during evaporation.

FIG. 29 schematically shows a fluorescence spectrum measurement system during evaporation. Light (193 nm in wavelength) emitted from an ArF excimer laser 29 was converged by an $SiO_2$ lens 28 (Sigma Koki Co., Ltd.) to a nail sample 27 while fluorescence 36 was guided by a $BaF_2$ lens (Ohyo Koken Co., Ltd., Tokyo) 35 and a UV grade fiber 34 and measured by a cooled CCD spectrometer, BTC-112 E (B&W TEK, USA) 32. To observe pulse light emission, a pulse delay generator DG535 (Stanford Research System, USA) 31 was employed to set a trigger delay between the excimer laser 29 and the cooled CCD spectrometer 32. To match the impedance, an attenuator 30 (10 dB) was provided.

Figure 30:
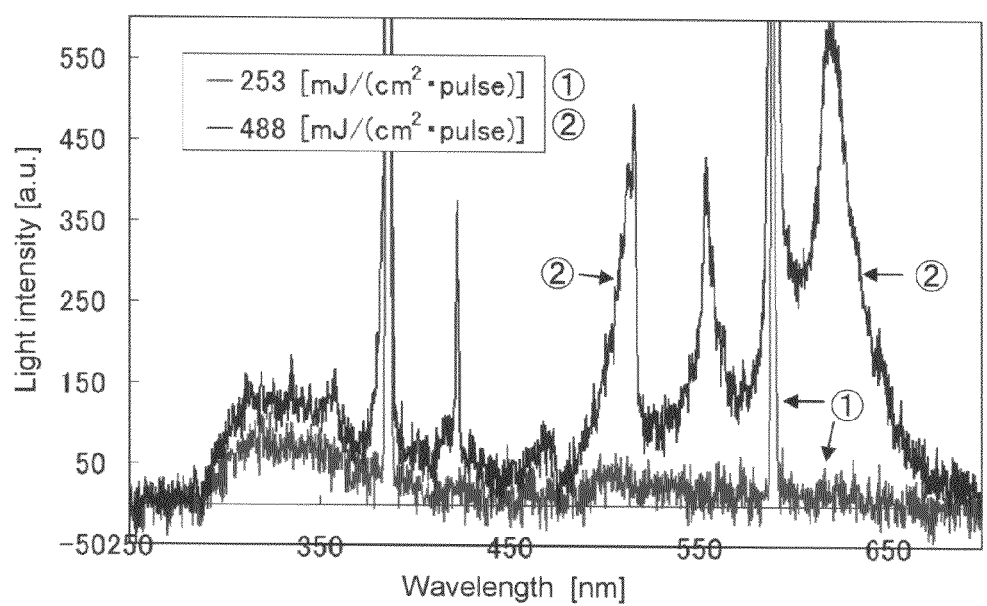
FIG. 30 shows light emission spectra (average of 10 times) of the nail irradiated with different irradiation energy densities.
Figure 31:
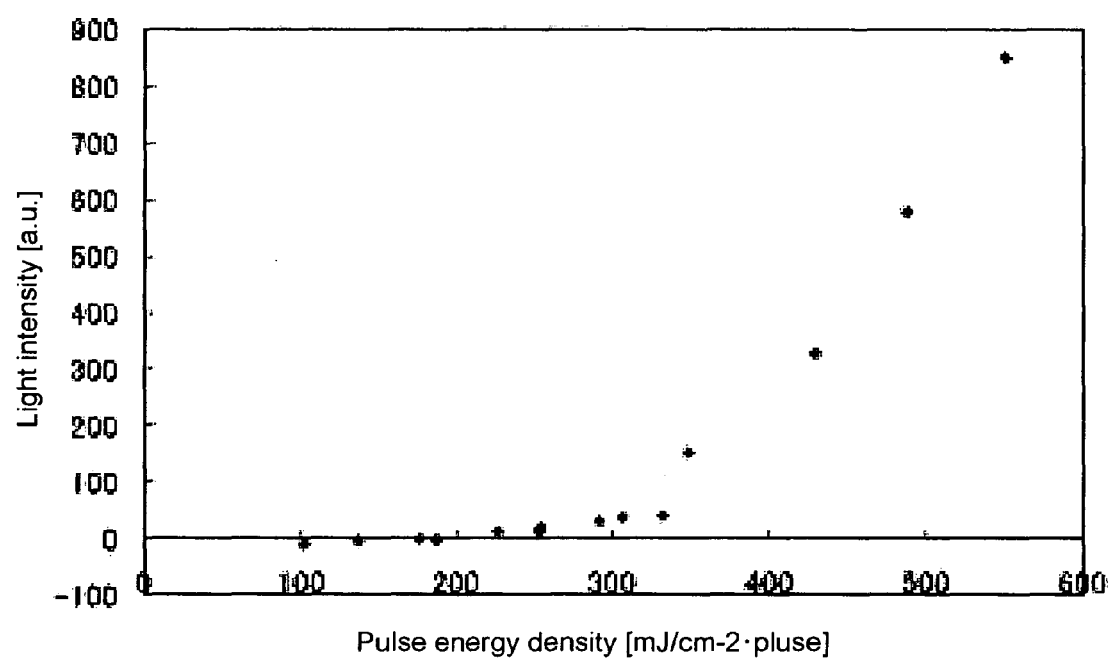
FIG. 31 is a graph showing dependency of plume emission amount (620 nm) upon intensity of excitation light.
Figure 32:
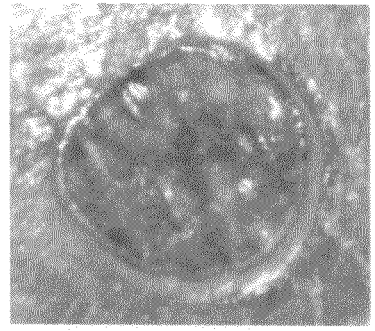
FIG. 32 shows the surface of the evaporated nail plate after irradiation at irradiation energy density of 226 $mJ/cm^{-2}$·pulse.

FIG. 30 shows emission spectra different in irradiation energy density. The light emission at a wavelength of near 300 nm to 350 nm is fluorescence due to a nail protein. The light at a wavelength of 386 nm is scattered light due to discharge in excitation light. Several emission peaks observed in a long wavelength side larger than 400 nm are due to plume. As the irradiation energy increases, the intensity of light emitted by plume increases. When the intensity of one (620 nm) of the emission peaks is used as a reference for plume emission intensity, the emission intensity of plume is found to abruptly increase when a pulse energy density exceeds 300 mJ/($cm^{-2}$·pulse). This suggests that to perform fluorescence measurement under less effect of plume emission, irradiation must be performed at an irradiation energy density of 300 mJ/($cm^{-2}$·pulse) or less. FIG. 31 shows the dependency of plume emission amount (620 nm) upon the intensity of excitation light. FIG. 32 shows the surface state at an irradiation energy density of 226 mJ/($cm^{-2}$·pulse), and Table 2 shows the relationship between irradiation energy density and evaporation depth. From this, it is suggested that the surface state is flat even at an irradiation energy density of 300 mJ/($cm^{-2}$·pulse) and that a probe is satisfactorily fixed when glucose is measured through the nail plate. Furthermore, as to the evaporation depth, it is suggested that about 1800 irradiation times is required to evaporate the nail plate to make a hole almost in contact with the nail bed portion. The number of irradiation times corresponds to a processing time of several minutes.

TABLE 2

Relationship between irradiation energy density and evaporation depth

| Energy density [mJ/$cm^2$ · pulse] | Evaporation depth [μm] | Number of irradiation times to form a through-hole of 400 μm in the nail |
|---|---|---|
| 265 | 0.22 | 1818 |
| 530 | 0.36 | 1111 |
| 935 | 0.46 | 869 |

(2-2) Comparison in Fluorescence Spectrum Between the nail Plate and the Dermis

To find a difference between fluorescence emitted from the nail plate and that from the dermis under the nail, spectrum of the nail plate and that of the swine dermis (used as a model of the dermis) were measured.

Using the measurement system shown in FIG. 29, fluorescence spectra were measured with respect to the nail and the swine dermis at an irradiation energy density of 257 mJ/($cm^{-2}$·pulse).

Figure 33:
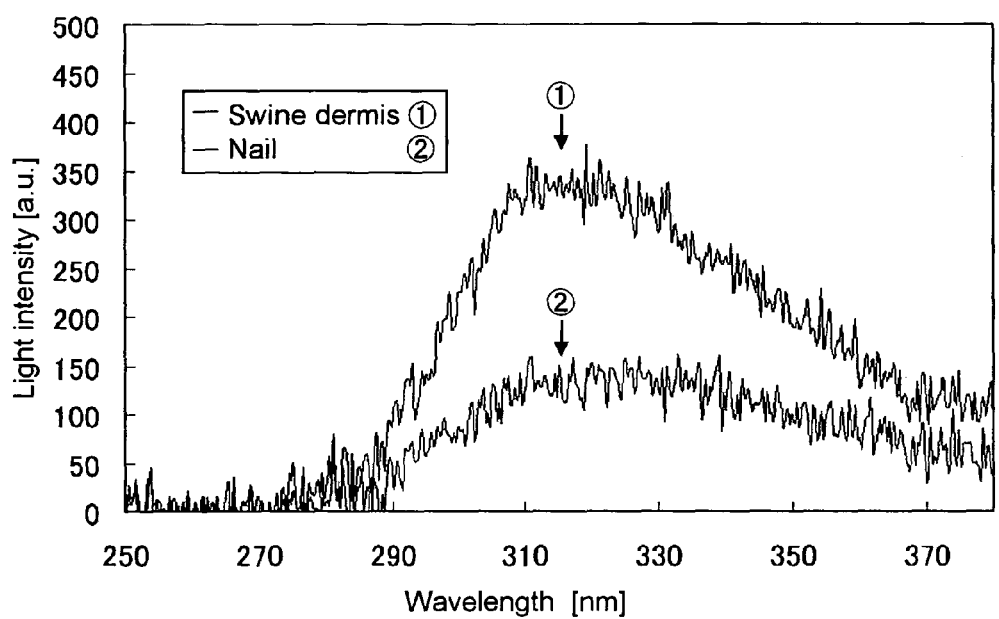
FIG. 33 shows a fluorescence spectrum of the swine dermis in comparison with that of the nail (257 $mJ/cm^2$·pulse, 10 times in average)

The spectra of them are shown in FIG. 33. There is less difference in wavelength between fluorescence spectra of the nail plate and the dermis; however, the intensity of fluorescence emitted from the swine dermis is two fold larger than that of the nail plate. It is suggested that the border line between the nail plate and the dermis can be found by observing the intensity of fluorescence of 300 to 350 nm during evaporation.

Example 5

Glucose Measurement Through the Nail Plate

Figure 34:
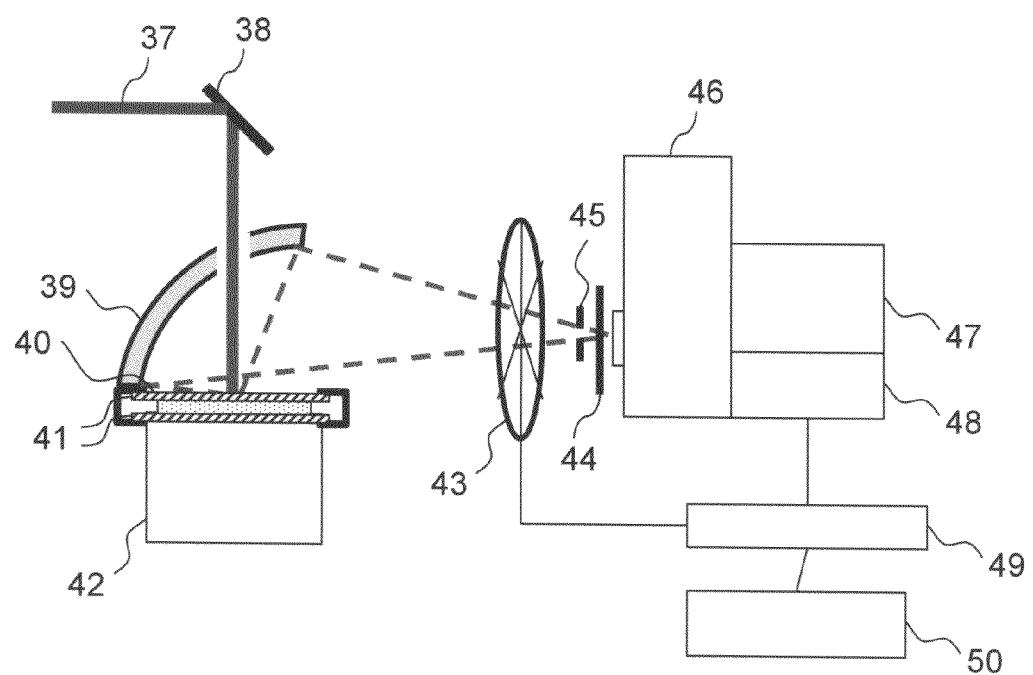
FIG. 34 schematically shows a measurement system for reflectivity of light diffused from a glucose solution under the nail plate.

As shown in FIG. 34, light 37 having a wavelength of 2.1 μm was applied to a sample by means of an aluminum flat mirror 38. The reflected light thereof was converged by means of an elliptic mirror coated with gold (manufactured by Yamada Kogaku Kogyo, Saitama, Japan) 39 and detected by an MCT detector, KMPC12-2-JI (Kolmar Technologies Inc., USA) 46. To remove noise by infrared irradiation, a BK7 optical base (Sigma Koki Co., Ltd., Tokyo) 44 whose transmission wavelength range was 0.32 to 2.6 μm was provided. The detection light was chopped by an optical chopper (manufactured by N.F. Circuit Design Block Co., Ltd., Kanagawa, Japan) 43 at a frequency of 573 Hz., and amplified by a lock-in amplifier, L15630 (manufactured by N.F. Circuit Design Block Co., Ltd., Kanagawa, Japan) 49 and output in an oscilloscope DL708E (Yokokawa Electric Corporation, Tokyo) 50.

A solution sample 42 was prepared by using a 20% aqueous intralipid solution, intralipos 20% (Otsuka Pharmaceutical Co., Ltd., Tokyo) as a scattering body. On the solution, the nail 40 sandwiched by cover glasses 41 was mounted. The nail sample was prepared by taking the nail (9 mm×6 mm) of a ring finger of a 23 year-old woman and polishing both surfaces of the nail with sand paper P1000 (JIS standard B6010) to control the thickness. The reflected light amount when water was used as the solution was regarded as diffused/reflected light from the nail. The amount of diffused/reflected light from the nail was subtracted from that when the 20% aqueous intralipid solution was used to obtain the amount of diffused/reflected light from the solution. Then, the diffused/reflected light from the 20% aqueous intralipid solution containing 10 g/dL glucose was measured to obtain absorbance of glucose.

Figure 35:
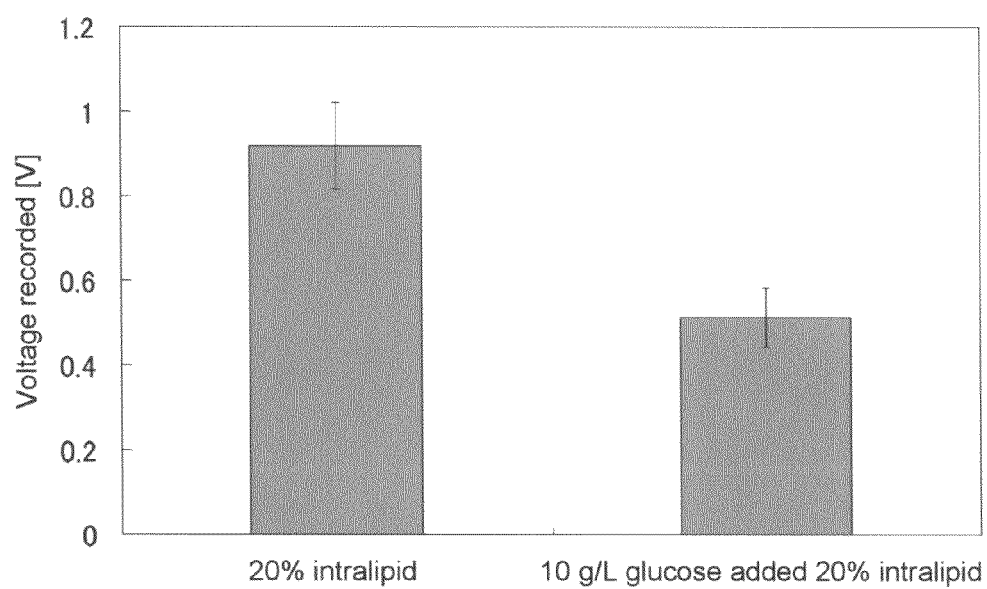
FIG. 35 is a graph showing the output (n=5) of the light diffused and reflected from a 20% intralipid solution in the presence or absence of glucose.

When the nail of 109 μm thick (which was reduced in thickness by polishing) was measured, the amount of the diffused/reflected light from the solution increased by 0.44 μW, compared to the nail (untreated ring-finger nail) of 337 μm thick. FIG. 35 shows the difference in diffused/reflected light amount in the presence or absence of glucose when the thickness of the nail is 109 μm. When 10 g/dL glucose is existing in 20% aqueous intralipid solution, the amount of the light diffused/reflected from the solution decreases and absorption of light by glucose is detected through the nail.

It was demonstrated that the detectable amount of the diffused/reflected light from the portion under the nail plate is increased by reducing the nail plate in thickness and thus glucose can be measured.

What is claimed is:

1. A device for optically measuring a test substance in blood by using a nail as an optical window which comprises:
   (i) a nail plate evaporation device, which partly removes a nail plate by evaporating the nail plate for creating an optical window in the nail, which comprises (a) a light generator generating a coherent light, (b) an evaporation depth monitor having a light detector detecting fluorescence emitted from the nail plate and the dermis for monitoring evaporation depth of the nail plate, and a controller which processes the detected fluorescence to determine evaporation depth information of the nail plate for controlling the light generator;
   (ii) an irradiator configured to apply light within a wavelength range for measuring absorption by the test substance through the optical window;
   (iii) a detector configured to detect light diffused/reflected from or transmitted through the body of a subject;
   (iv) a processor configured to process a signal obtained by the detector to convert the signal into a concentration of the test substance;
   (v) a monitor configured to monitor a water content and a keratin content of the nail by using light within a wavelength range for measuring absorption by water in the nail and light within a wavelength range for measuring absorption by keratin in the nail to correct or eliminate optical characteristics of the nail plate in the detected light.

2. The device according to claim 1, wherein the irradiator and the detector are contained in a probe, and light is applied by the irradiator through the nail into the body of the subject and light diffused/reflected from the body of the subject is detected by the detector through the nail.

3. The device according to claim 1, wherein the irradiator applying light within a wavelength range for measuring absorption by the test substance to the nail applies light to capillary vessel of the nail bed portion.

4. The device according to claim 1, wherein the irradiator applying light within a wavelength range for measuring absorption by the test substance to the nail applies near infrared light.

5. The device according to claim 4, wherein the wavelength range of the light to be applied is 1 to 2.5 μm.

6. The device according to claim 1, wherein the device is a blood glucose level measuring device.

7. The device according to claim 1, wherein the device is used for measuring blood urea, creatinine, BUN, or CP (creatinine phosphokinase).

8. The device according to claim 1, wherein the monitor uses light having a wavelength of 1 to 3 μm as the light within a wavelength range for measuring absorption by water in the nail and light having a wavelength of 1 to 2.5 μm as the light within a wavelength range for measuring absorption by keratin in the nail.

9. The device according to claim 1, wherein the coherent light source is ultraviolet laser light or OPO.

10. The device according to claim 9, wherein the ultraviolet laser light is ArF laser light.

11. The device according to claim 1, wherein a pulse energy density of the coherent light from the light generator is not less than 10 mJ/cm$^2$·pulse.

12. The device according to claim 1, wherein, in monitoring the evaporation depth of the nail plate, irradiation is performed with a fluence such that intensity of plume emission, which is simultaneously generated in a wavelength range of fluorescence generating during light irradiation for evaporation, is equal to or less than intensity of fluorescence emitted from the nail plate and/or the dermis.

13. The device according to claim 1, further comprising a holder of a finger tip portion, which has the laser light irradiator and the light detector.

* * * * *